US009194801B2

(12) United States Patent
Shepard et al.

(10) Patent No.: US 9,194,801 B2
(45) Date of Patent: Nov. 24, 2015

(54) SYSTEMS AND METHODS FOR A DNA-BASED THERMOMETER

(75) Inventors: Kenneth L. Shepard, Ossining, NY (US); Ioannis Kymissis, New York, NY (US); Haig Norian, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/595,106

(22) Filed: Aug. 27, 2012

(65) Prior Publication Data

US 2013/0224879 A1   Aug. 29, 2013

Related U.S. Application Data

(60) Provisional application No. 61/527,674, filed on Aug. 26, 2011.

(51) Int. Cl.
*G01N 25/00* (2006.01)
*G01N 21/64* (2006.01)
*B01J 19/00* (2006.01)
*G01K 11/20* (2006.01)

(52) U.S. Cl.
CPC ......... *G01N 21/6486* (2013.01); *B01J 19/0046* (2013.01); *G01K 11/20* (2013.01); *G01K 2213/00* (2013.01); *G01N 21/6428* (2013.01)

(58) Field of Classification Search
CPC ............ G01N 21/6486; G01N 21/6428; B01J 19/0046; G01K 11/20
See application file for complete search history.

(56) References Cited

U.S. PATENT DOCUMENTS

| 5,599,668 | A | * | 2/1997 | Stimpson et al. ............ 435/6.11 |
| 6,030,115 | A |   | 2/2000 | Ishiguro et al. |
| 2002/0022226 | A1 |   | 2/2002 | Nakao et al. |
| 2003/0087292 | A1 | * | 5/2003 | Chen et al. ......................... 435/6 |
| 2005/0145496 | A1 | * | 7/2005 | Goodsaid et al. ............ 204/600 |

OTHER PUBLICATIONS

Barilero et al "FLuorescent thermometers for dual-emission wavelength measurements: Molecular engineering and application to thermal imaging in a microsystem" Analytical Chemistry, 2009, 81(19): 7988-8000.*
Barilero et al Analytical Chemistry, 2009, 81: supplemental information.*
Arata, et al., "Millisecond Analysis of Double Stranded DNA with Flourescent Intercalator by Micro-Thermocontrol-Device", *Talanta*, 79(3):963-966 (2009).

(Continued)

*Primary Examiner* — Betty Forman
(74) *Attorney, Agent, or Firm* — Baker Botts L.L.P.

(57) ABSTRACT

DNA-based temperature sensor for measuring temperature through a transition of one or more strands of DNA from a coupled configuration to a decoupled configuration at a temperature threshold, and a fluorescent dye adapted to emit fluorescence when the DNA is in the coupled configuration, includes a receptacle adapted to receive the DNA and the fluorescent dye in a solution, an imaging device adapted to acquire an image of fluorescence emitted from the solution, the image having a plurality of regions, and a processor adapted to determine a plurality of fluorescence levels corresponding to each of the plurality of regions of the image and to generate a temperature map based on the determined fluorescence levels. A method for measuring temperature and a DNA-based temperature sensing solution are also provided.

20 Claims, 33 Drawing Sheets
(33 of 33 Drawing Sheet(s) Filed in Color)

(56) References Cited

OTHER PUBLICATIONS

Gudnason, et al., "Comparison of Multiple DNA Dyes for Real-Time PCR: Effects of Dye Concentration and Sequence Composition on DNA Amplification and Melting Temperature", *Nucleic Acids Reasearch*, 35(19):e127 (2007).

Tashiro, et al., "A Nanothermometer Based on the Different pi Stacking of B- and Z-DNA", *Angewandte Chemie International Edition*, 42(18):6018-6020 (2003).

Tashiro, et al., "The Molecular-Thermometer Based on B-Z- Transition of DNA", *Nucleic Acids Symposium Series*, 48(1):89-90 (2004).

* cited by examiner

```
                      SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: for the exemplary sequence, a temperature
      bandwidth of approximately 10 degrees Celsius is centered at a
      melting temperature of 72.6 degrees Celsius

<400> SEQUENCE: 1
aaaggaaagg aaaaggaaaa gg                                            22
```

SYSTEMS AND METHODS FOR A DNA-BASED THERMOMETER

CROSS-REFERENCE TO RELATED APPLICATIONS

This application claims priority to U.S. Provisional Patent Application Ser. No. 61/527,674, filed on Aug. 26, 2011, the disclosure of which is incorporated by reference herein in its entirety.

INCORPORATION BY REFERENCE OF A SEQUENCE LISTING

A Sequence Listing is included pursuant to 37 C.F.R. 1.821. The Sequence Listing was submitted via EFS-Web on Apr. 12, 2013. The Sequence Listing includes the ASCII text file 0700504632seq.txt, which is 668 bytes in size and was created on Apr. 12, 2013, and which is incorporated by reference herein in its entirety. The Sequence Listing does not include any new matter which goes beyond the disclosure of the application as filed.

BACKGROUND

With the miniaturization of bioanalytic tools, such as droplet-based PCR and temperature-gradient gel electrophoresis, precise determination of temperature in small volumes is desirable.

Certain measurement techniques, such as resistance temperature detectors, microthermocouples, cholesteric liquid crystals and infrared temperature profilometry can be unable to provide adequate temperature and spatial resolution to allow for the reliable characterization of these devices. In addition, certain detection approaches, such as resistance temperature detectors (RTDs) and thermocouples, can produce a heat load from the sensor itself. Infrared detectors, particularly those with large enough germanium lenses and suitably dense sensor arrays, can provide sub-micron spatial resolution, but generally offer limited temperature resolution on the order of 2-3 degrees Celsius, and can have difficulties in determining a room-temperature baseline. Cholesteric liquid crystals can achieve both high temperature and spatial resolution but can also be relatively complex in application, at least in part due to the application including treating the surface with a black paint primer prior to output wavelength detection.

There is a need for improved temperature sensors that avoid these issues.

SUMMARY

Systems and methods for DNA-based temperature sensors are provided herein.

The disclosed subject matter provides DNA-based temperature sensors and techniques for DNA-based temperature sensing. In certain embodiments, the disclosed subject matter provides a sensor for measuring temperature through a transition of one or more strands of DNA from a coupled configuration to a decoupled configuration at a temperature threshold, and a fluorescent dye adapted to emit fluorescence when the DNA is in the coupled configuration. The sensor can include a receptacle adapted to receive the DNA and the fluorescent dye in a solution, an imaging device adapted to acquire an image of fluorescence emitted from the solution, and a processor adapted to determine a plurality of fluorescence levels corresponding to each region in the image and to generate a temperature map based on determined fluorescence levels.

In some embodiments, the receptacle can include a polydimethylsiloxane gasket disposed about the perimeter of the receptacle.

In some embodiments, the sensor can include a light source optically coupled to the receptacle. The sensor can include an excitation filter optically coupled to the light source and the receptacle and adapted to filter light from the light source to emit an excitation light. The sensor can include a reflective element adapted to optically couple the excitation light with the receptacle. The sensor can include an optical element optically coupled to the excitation filter and the receptacle and adapted to focus the excitation light onto the receptacle, and in some embodiments, the optical element can be an objective lens.

In some embodiments, the sensor can include an emission filter optically coupled to the receptacle and the imaging device and adapted to filter noise from the emitted fluorescence. The sensor can include an optical element optically coupled to the receptacle and the imaging device and adapted to focus the emitted fluorescence onto the imaging device, and in some embodiments, the optical element can be an ocular lens.

In some embodiments, the solution can include 1 part of fluorescent dye and about 1 part of 800 µM of DNA strands in 1× phosphate buffered saline. In some embodiments, the DNA can include a DNA sequence represented as AAAG-GAAAGGAAAAGGAAAAGG (SEQ ID NO: 1) and/or a reverse complement thereof.

The disclosed subject matter also provides methods for measuring temperature of a subject through a transition of one or more strands of DNA from a coupled configuration to a decoupled configuration. In certain embodiments, example methods include receiving a solution including the DNA as a suspension in phosphate buffered saline and a fluorescent dye adapted emit fluorescence when the DNA is in the coupled configuration, placing the solution in proximity to the subject to permit the transition of the DNA from the coupled configuration to the decoupled configuration if the temperature reaches a temperature threshold, acquiring an image of fluorescence emitted from the solution, if any, the image having a plurality of regions, determining a plurality of fluorescence levels corresponding to each of the plurality of regions of the image, and generating a temperature map based on the determined fluorescence levels.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

According to one aspect of the disclosed subject matter, a DNA-based temperature sensor 100 (as shown, for example in FIGS. 1A-1B) can be configured for measuring temperature through a transition of one or more strands of DNA from a coupled configuration to a decoupled configuration at a temperature threshold, and a fluorescent dye adapted to emit fluorescence when the DNA is in the coupled configuration. The disclosed subject matter can be utilized for temperature sensing in a wide variety of applications, including for example and without limitation, in lab-on-chip applications and biological systems.

Figure 1:
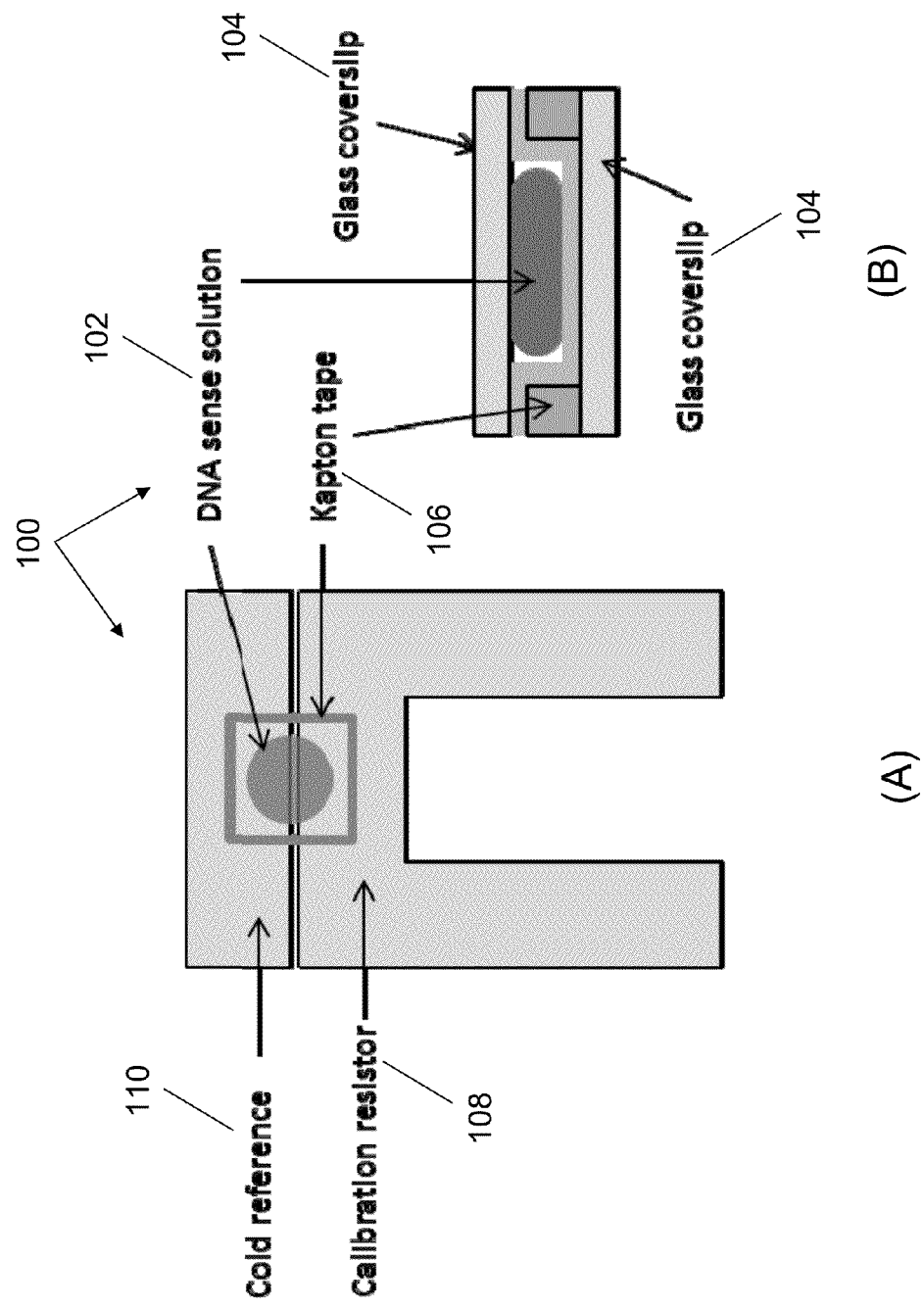
FIGS. 1A-1B are plan and front view diagrams, respectively, illustrating an exemplary DNA-based temperature sensor, in a calibration configuration, according to the disclosed subject matter.

FIGS. 1A-1B show an exemplary DNA-based temperature sensor 100 according to the disclosed subject matter. DNA oligonucleotides with a specified sequence can be synthesized using standard techniques (for example as performed by Eurofins or the like). For purpose of illustration and not limitation, dehydrated, complementary DNA strands can be suspended in a phosphate buffered solution (PBS 1×) to yield an 800 µM oligonucleotide solution. 50 µL of oligonucleotide solution can be mixed with 50 µL of intercalator dye (for example and as embodied herein, EvaGreen, 25 µM dye) to produce a DNA sensing solution 102. A 2.0 L droplet of DNA sensing solution 102 can be placed atop the device-under-test and covered with a glass coverslip 104. The glass coverslip 104 can be surrounded by polydimethylsiloxane, Kapton tape or the like to form a gasket 106. The thermal loading presented by the temperature sensing droplet can approximate the load that would be supplied by water upon a planar lab-on-chip device.

DNA-based temperature sensor 100 can utilize DNA melting, as tracked by an intercalator dye, to obtain a two-dimensional temperature profile. When excited with a broadband UV source, regions of high temperature can have a higher concentration of ssDNA, which can be identified by reduced fluorescent emission intensity from the intercalator dye. Through calibration of the DNA temperature sensing solution, a fluorescence-to-temperature mapping can be acquired. A single 12 base oligonucleotide can achieve a dynamic range of approximately 10° C. Several different oligonucleotides can also be combined in a single solution, to extend the dynamic range of the thermometer, for example from about 25° C. to 95° C.

To determine the dynamic range of the temperature sensor 100, a DNA oligonucleotide with a broad melting profile, as described above, can be configured. For purpose of illustration, commercially available DNA melting prediction software, such as DINAMelt from Nicholas R. Markham at Rensselaer Polytechnic Institute, can be used to simulate oligonucleotide melting. The DNA oligonucleotide can be selected to avoid strands that exhibit self-folding tendencies. As such, a strand can be created having a relatively highly linear melting profile over a specified temperature range, which for purpose of illustration and not limitation is set herein to be 10 degrees Celsius. Many factors can influence the melting temperature and its slope. For example, relatively long sequences (i.e., greater than about 50 bp) with a random assortment of nucleotides can have relatively high melting temperatures, for example about 94° C. Relatively shorter sequences (i.e., less than about 50 bp) can have lower melting temperatures. The slope of the melting curve can dependent on the sequence itself. Sequences having relatively high concentration of guanine-cytosine pairs can have broad melting curves, due at least in part to the strength of the inter-base bonds.

Figure 2:
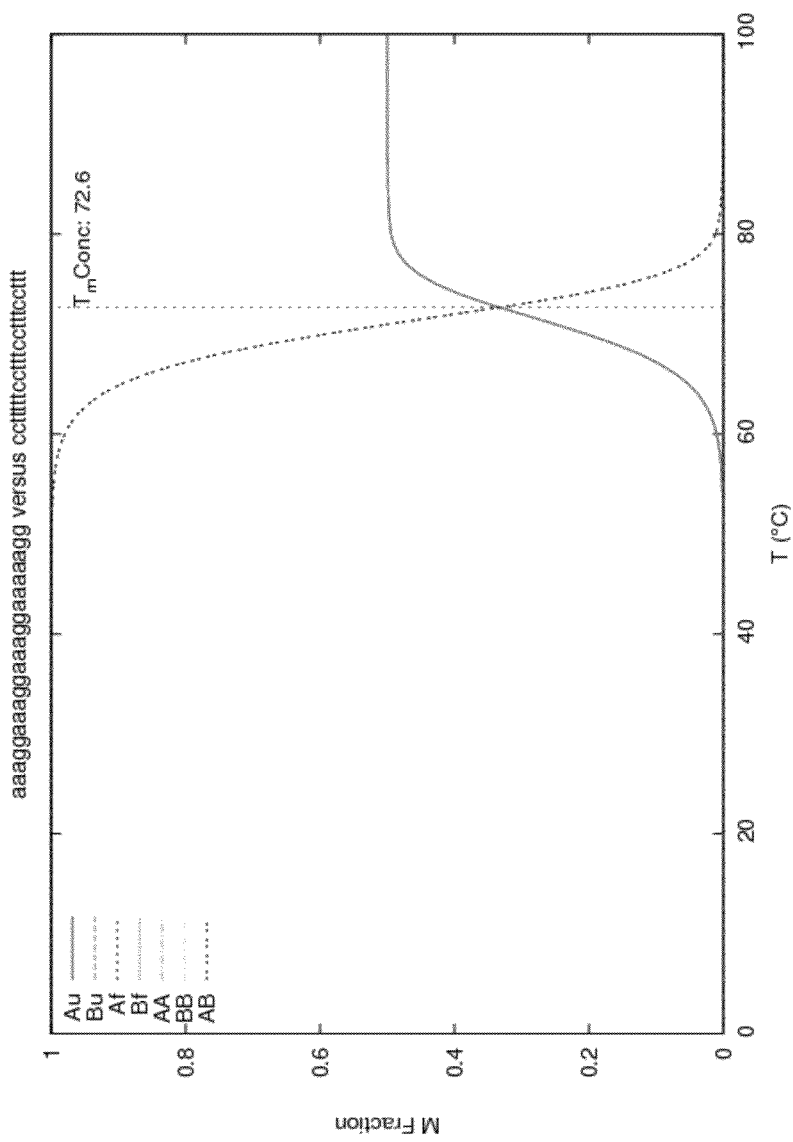
FIG. 2 is a diagram illustrating features of exemplary DNA sequences according to the disclosed subject matter.

A simulated melting curve is shown in FIG. 2 for an exemplary DNA sequence, represented as AAAGGAAAG-GAAAAGGAAAAGG (SEQ ID NO: 1). As shown in FIG. 2, for the exemplary sequence, a temperature bandwidth of approximately 10 degrees Celsius is centered at a melting temperature ($T_m$) of 72.6 degrees Celsius. Such simulations can provide an approximate dynamic range of the DNA melting temperatures for an exemplary DNA sequence.

Prior to obtaining a temperature profile of a given surface, the DNA sensor fluid can be calibrated on a calibration resistor 108, configured as a resistive element, embodied herein as a resistance temperature detector (RTD). For example, in the configuration shown in FIGS. 1A-1B, a constant voltage/current can be applied through a chrome-on-glass resistive trace for a duration of 120 seconds. The temperature of the center of the device can be recorded using a precision RTD (for example and as embodied herein, a PT100, F2020 RTD element from Omega Inc.), which can be accurate to about 0.1 degree Celsius. The DNA temperature sensing solution 102 (2 µL) can then be added to the center of the device, and the calibrated current values can be applied to the heater. A decrease of fluorescent intensity over time can be recorded using a CCD camera (for example and as embodied herein, a Hamamatsu ORCA-ER using IPLab software). An exemplary intercalator dye (for example and as embodied herein, EvaGreen) can be selected for the fluorescence microscopy and can have excitation/emission characteristics similar to that of fluoroescin isothiocyanate (FITC). As such, FITC lenses, having an excitation at about 480 nm and emission at about 530 nm, can be utilized to filter noise from the excitation and/or emission spectrum.

Substantially constant camera exposure time, gain, focus, droplet volume and droplet placement can be maintained to allow for relatively more consistent results. Each image captured by the camera can contain fluorescent information from the heated calibration resistor 108 zone and from a room temperature cold reference 110 zone. In this manner, a photobleaching correction can be made. That is, pixels in the hot region corresponding to the location where the RTD sensor was previously placed can be averaged to yield an average intensity for a given time, which can then be correlated to a temperature.

Figure 3:
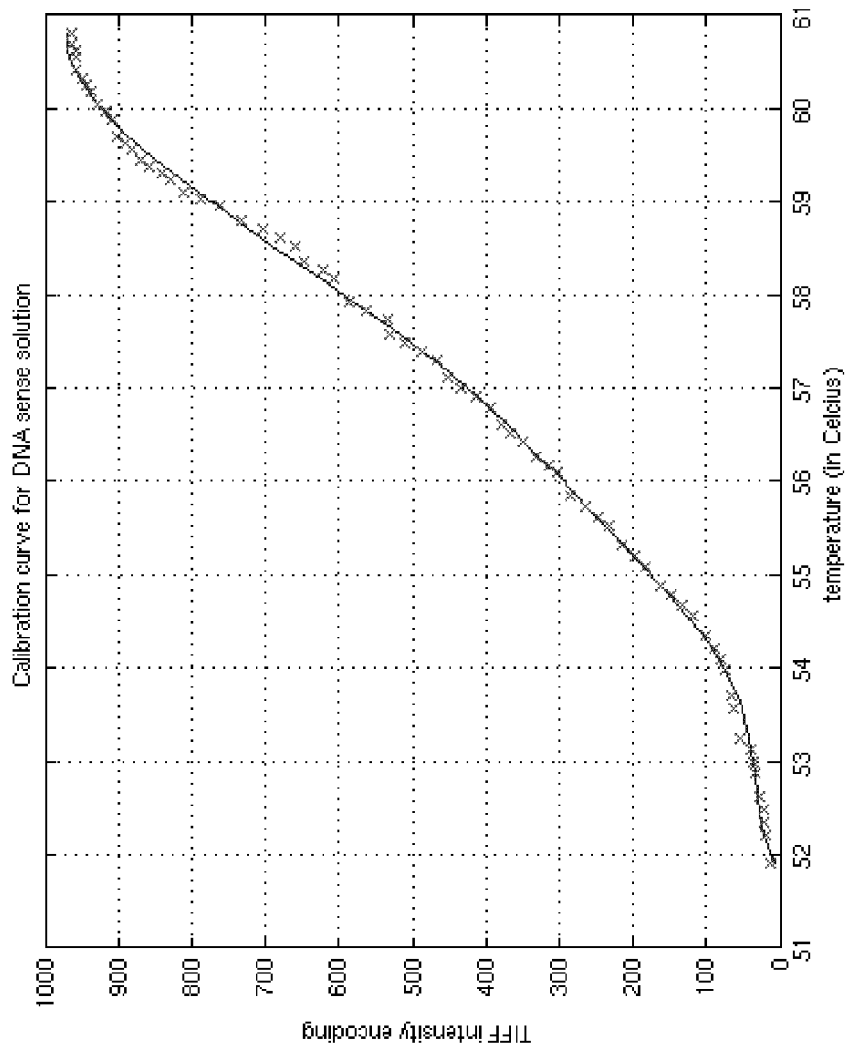
FIG. 3 is a diagram illustrating further features of the DNA-based temperature sensor of FIGS. 1A-1B.
Figure 4:
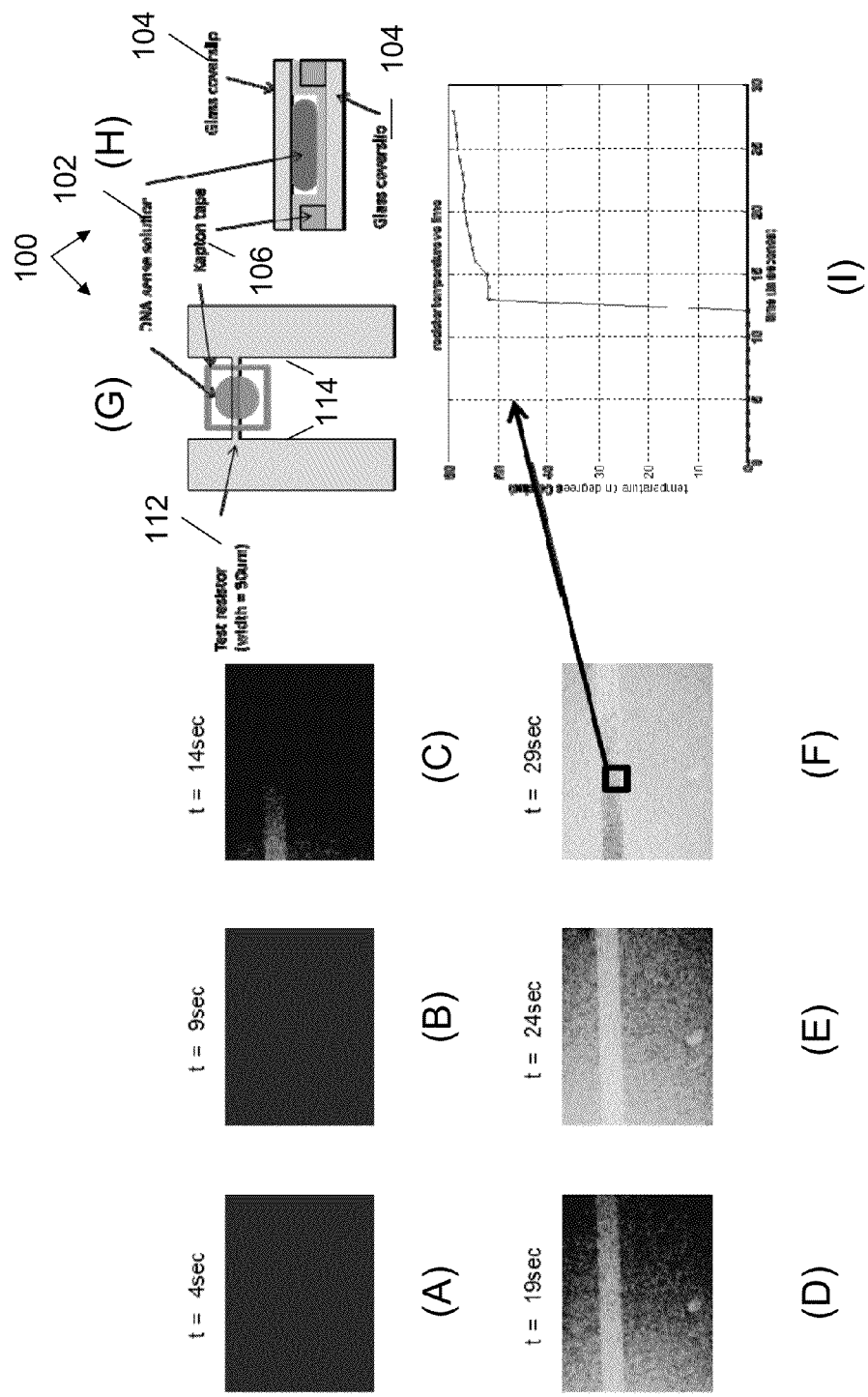
FIGS. 4A-4F are diagrams illustrating further features of the DNA-based temperature sensor of FIGS. 1A-1B.
FIGS. 4G-4H are plan and front view diagrams, respectively, of the exemplary DNA-based temperature sensor of FIGS. 1A-1B, in a measuring configuration.
FIG. 4I is a diagram illustrating further features of the DNA-based temperature sensor of FIGS. 1A-1B.

For the exemplary DNA temperature sensing solution described herein, the average intensity of the fluorescent light incident on the CCD as a function of temperature is shown in FIG. 3, along with deviation from the simulated DNA melting curve described above. Using the temperature mapping of FIG. 3, the temperature from the time-varying, two-dimensional photographs of the device-under-test can be determined. For the level of fluorescent excitation, the magnitude of the decrease in intercalator dye intensity can be independent of the time that the solution has been exposed, which can be shown by varying the delay between the turn-on of the UV source and the turn-on of the current source for the calibrator resistor.

Figure 5A:
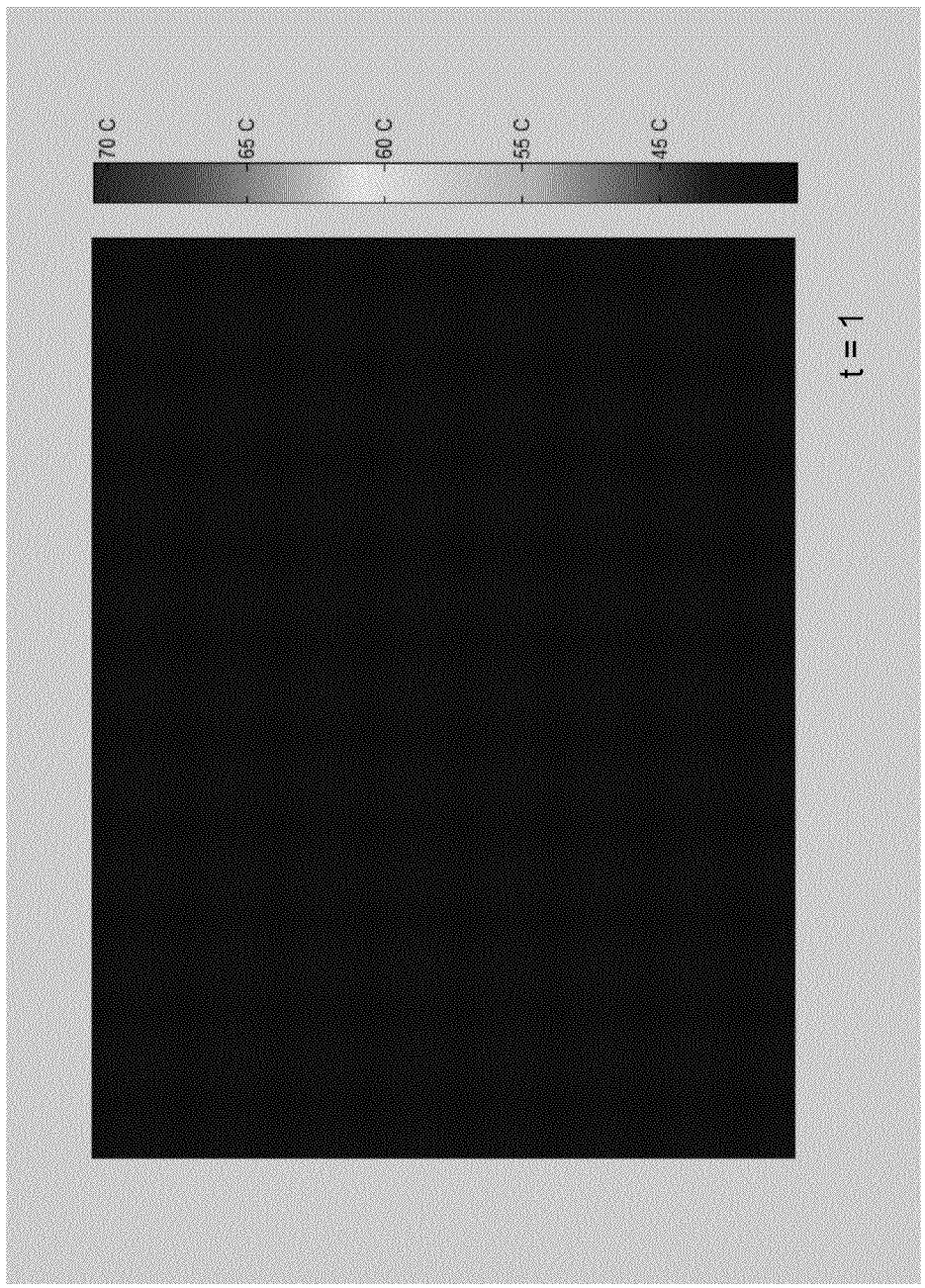
FIGS. 5A-5AC are diagrams illustrating further features of the DNA-based temperature sensor of FIGS. 1A-1B.
Figure 5B:
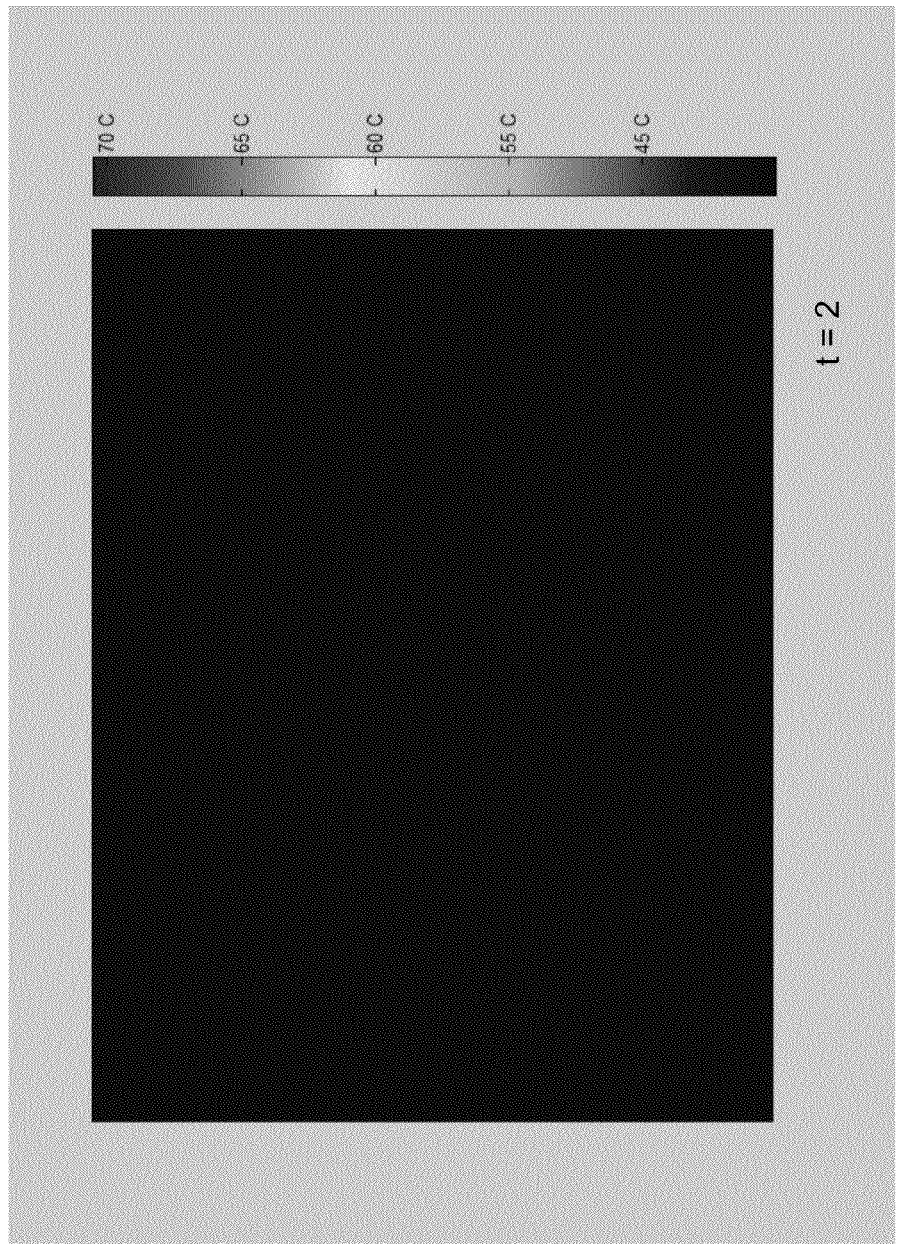
Figure 5C:
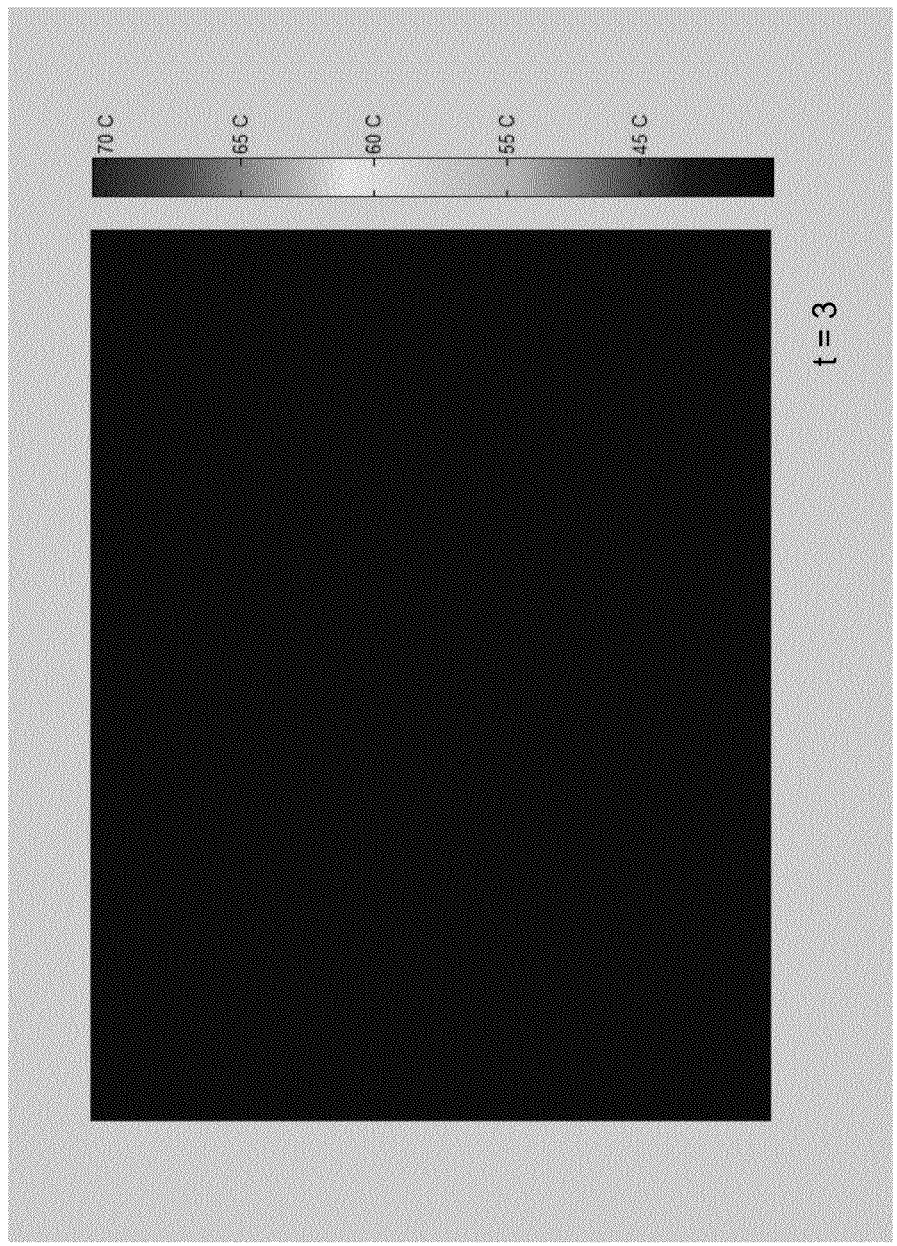
Figure 5D:
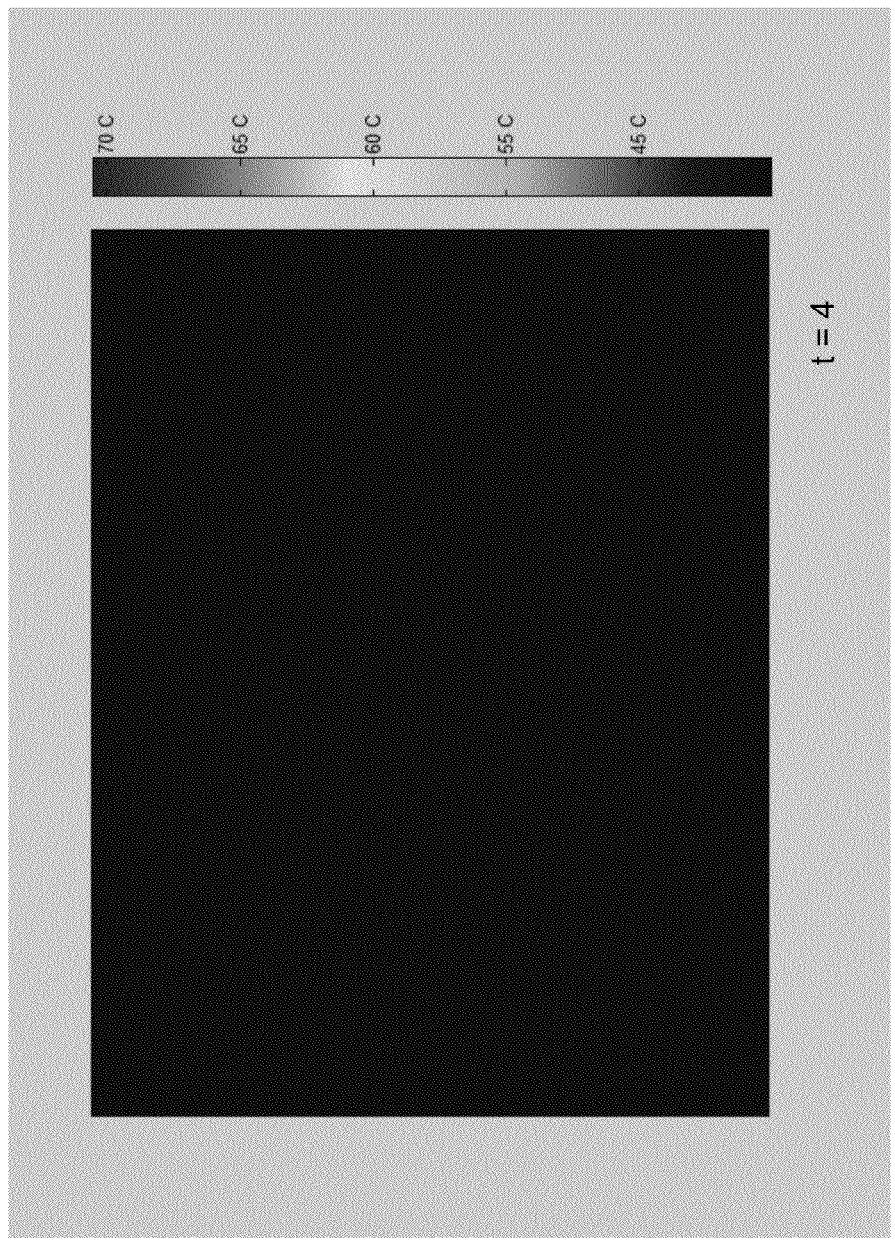
Figure 5E:
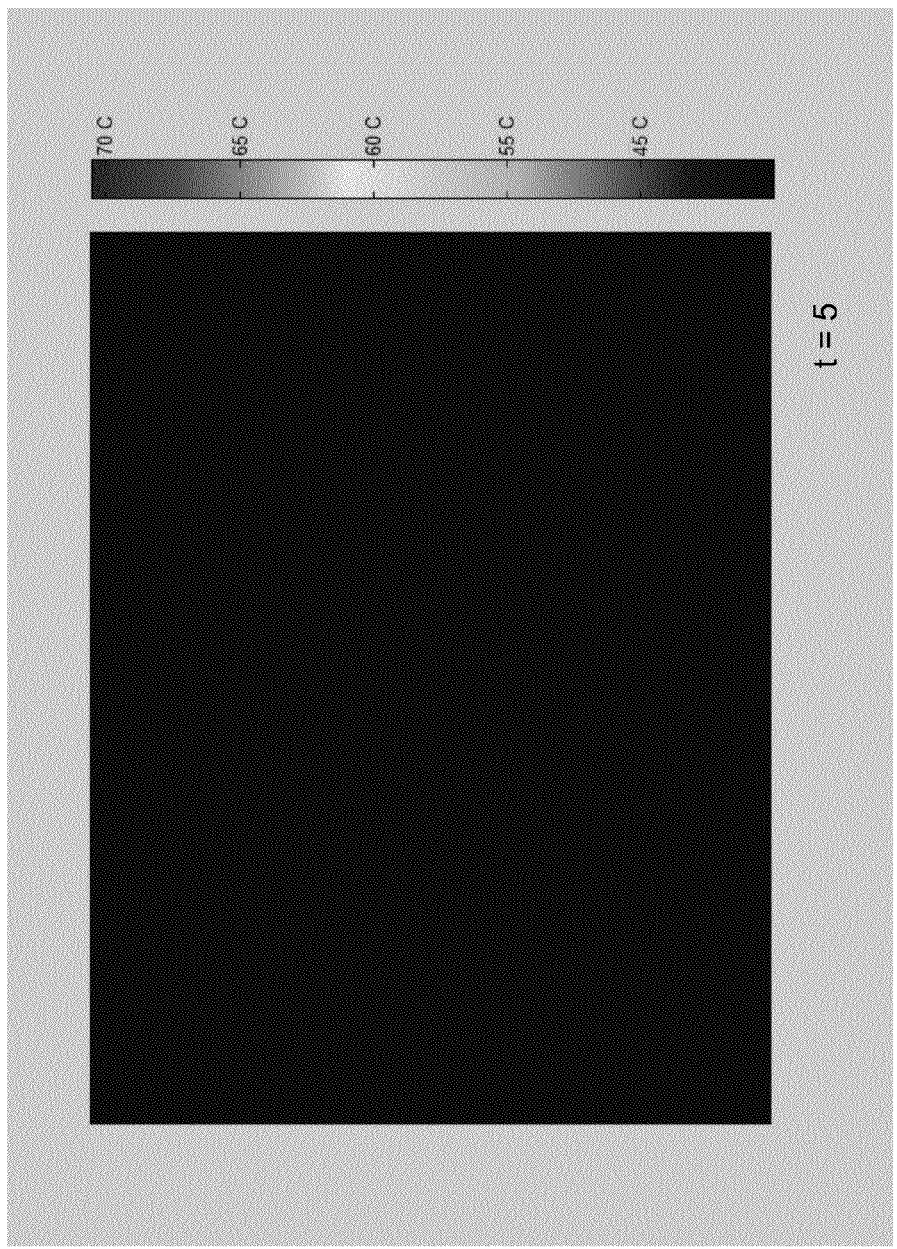
Figure 5F:
Figure 5G:
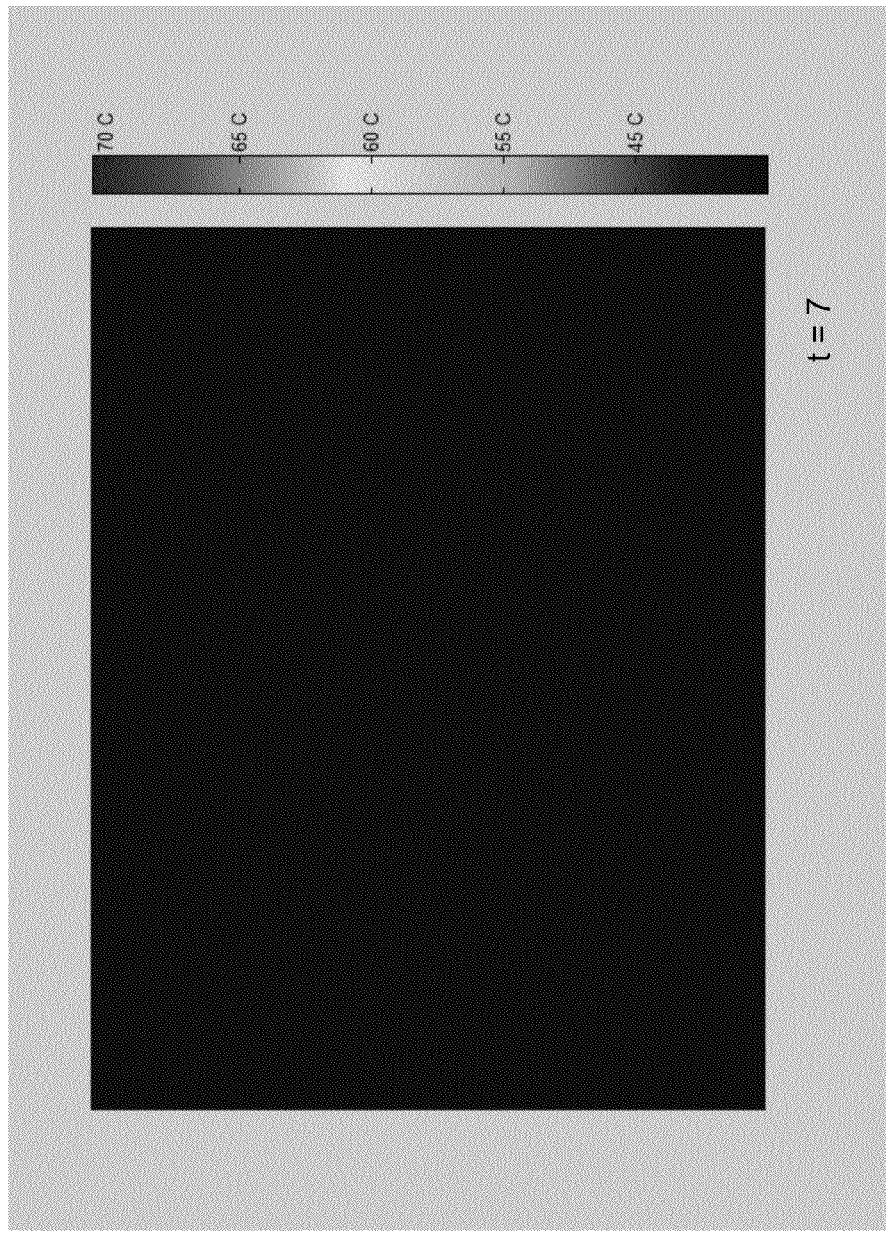
Figure 5H:
Figure 5I:
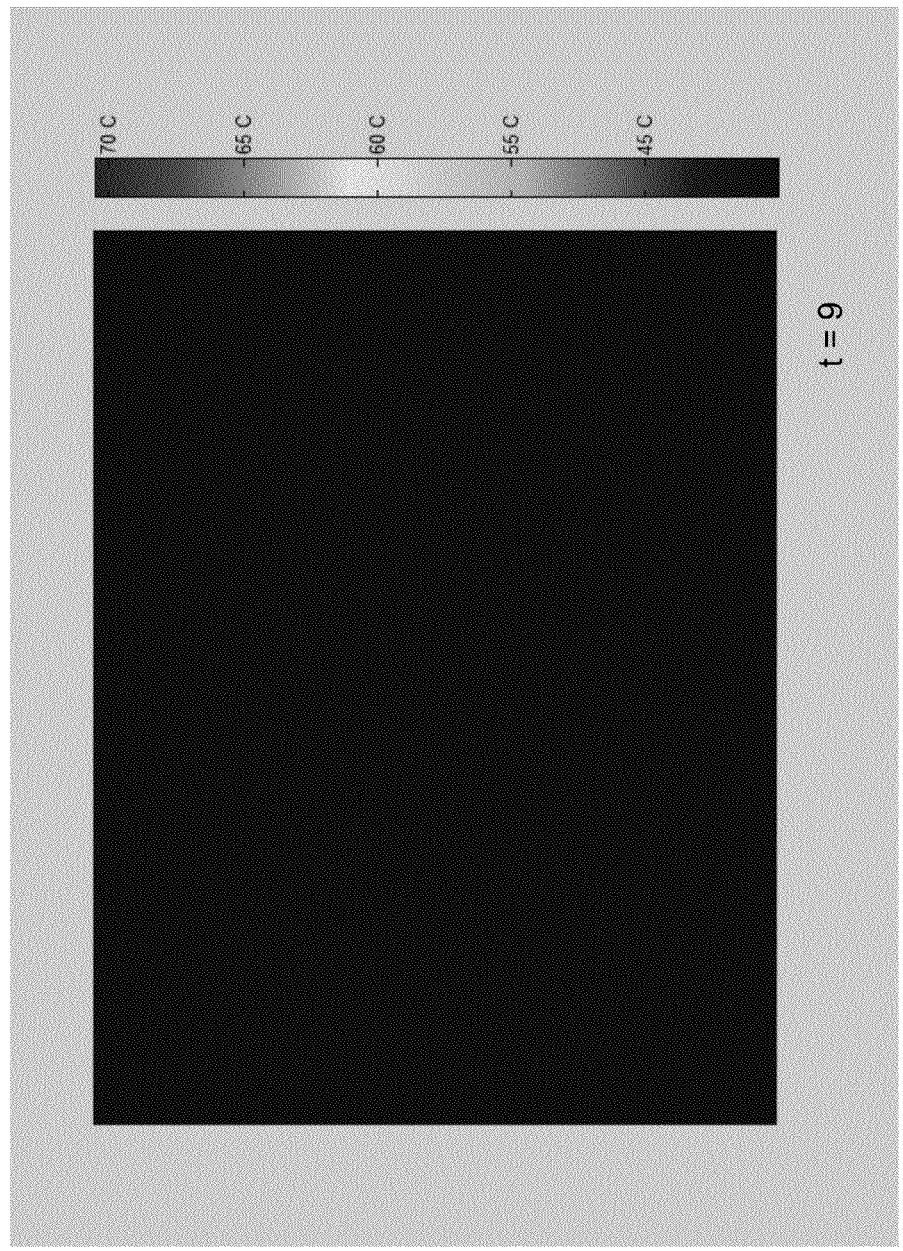
Figure 5J:
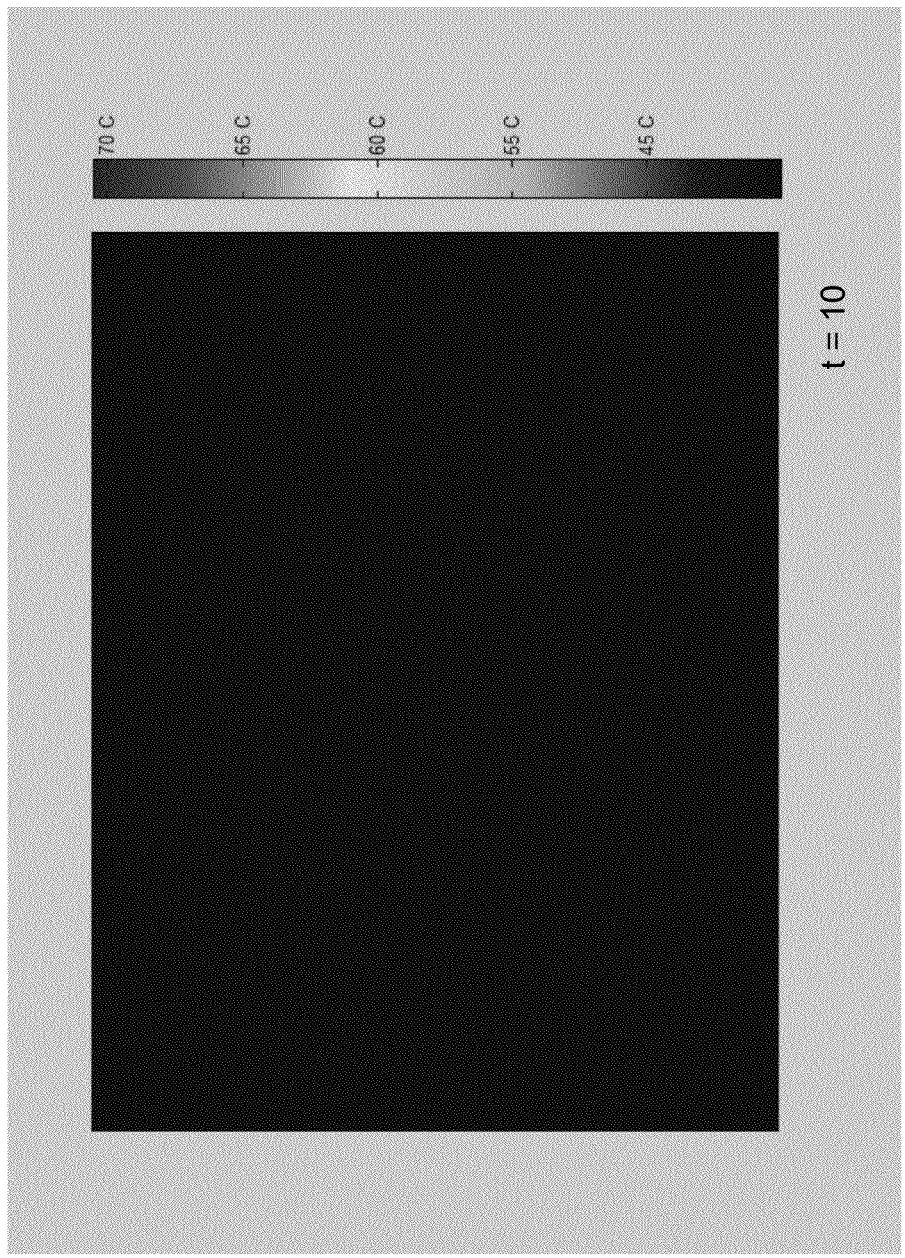
Figure 5K:
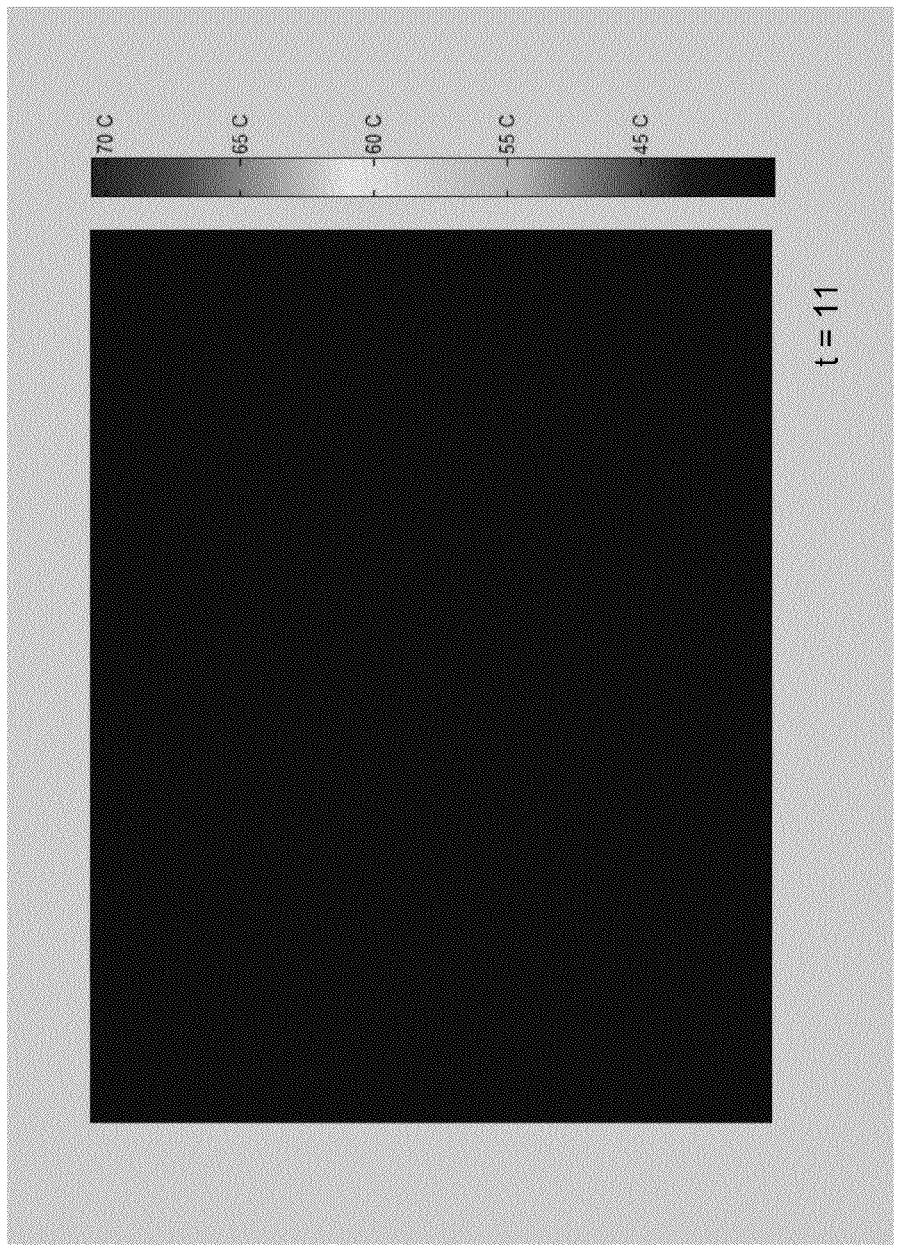
Figure 5L:
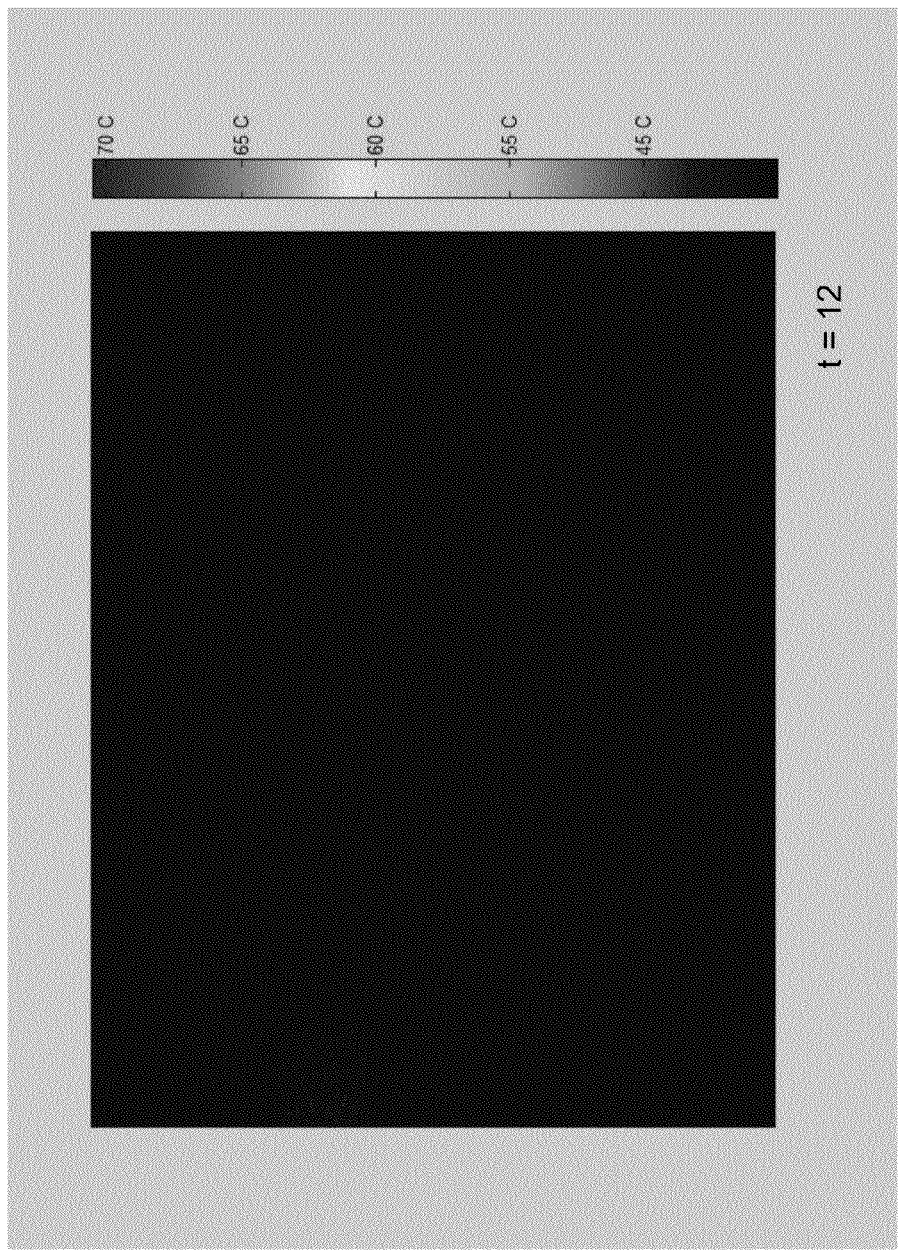
Figure 5M:
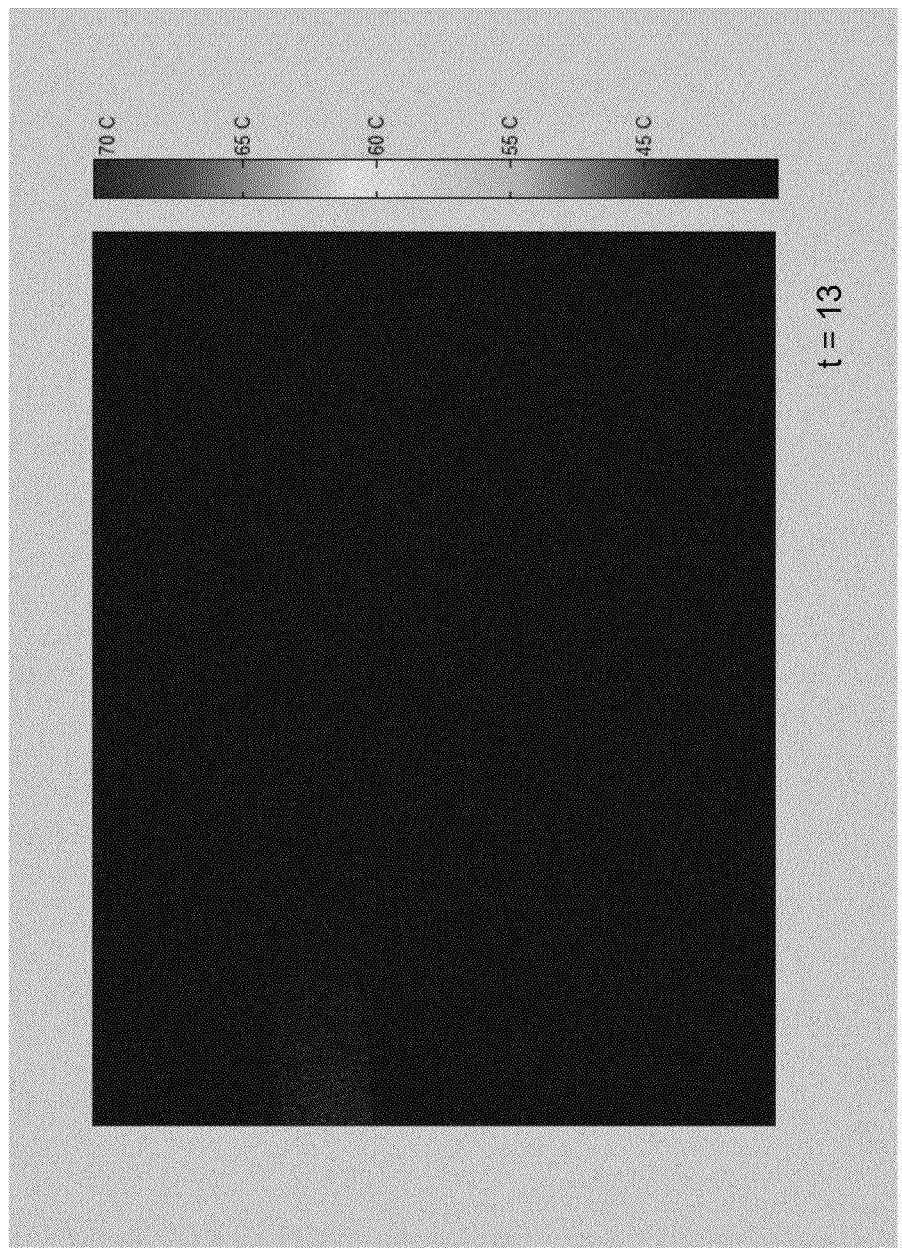
Figure 5N:
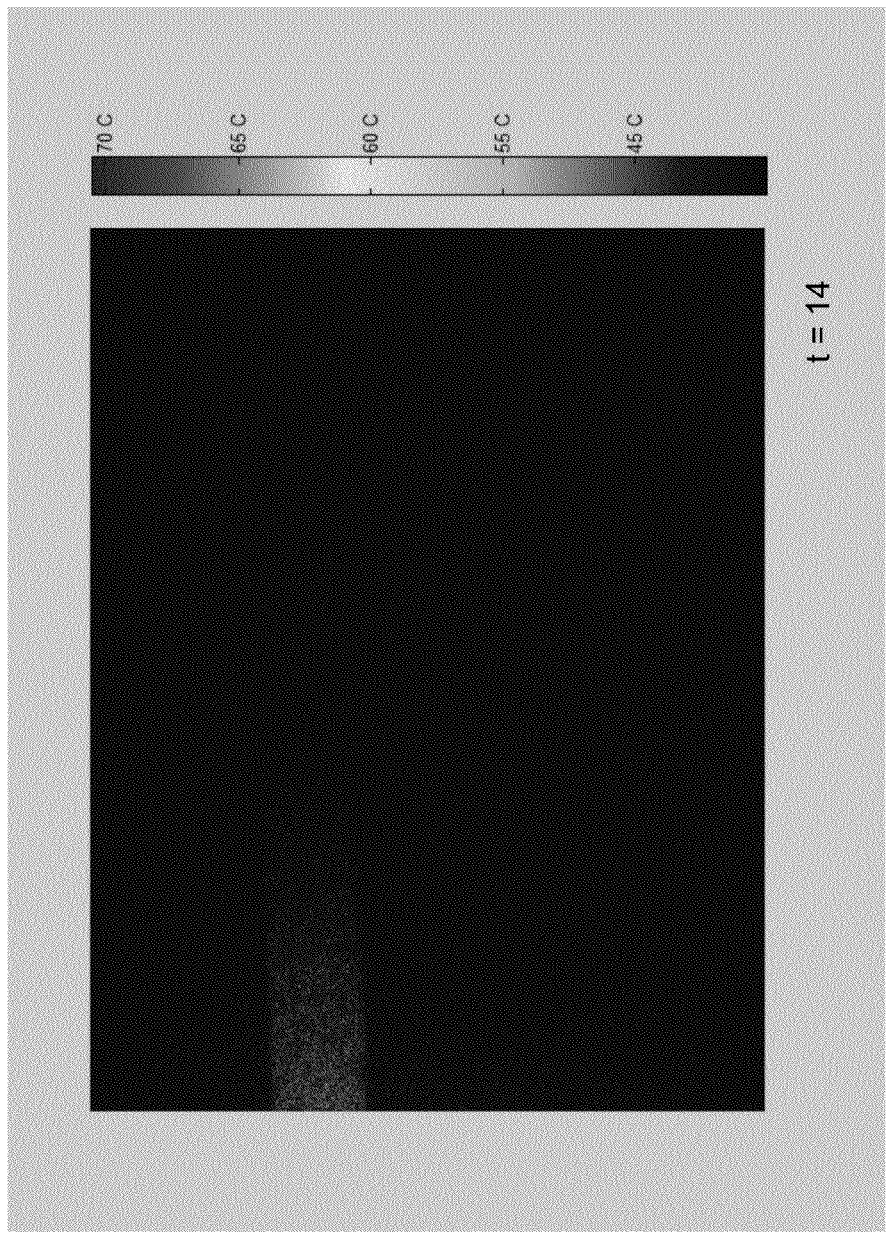
Figure 50:
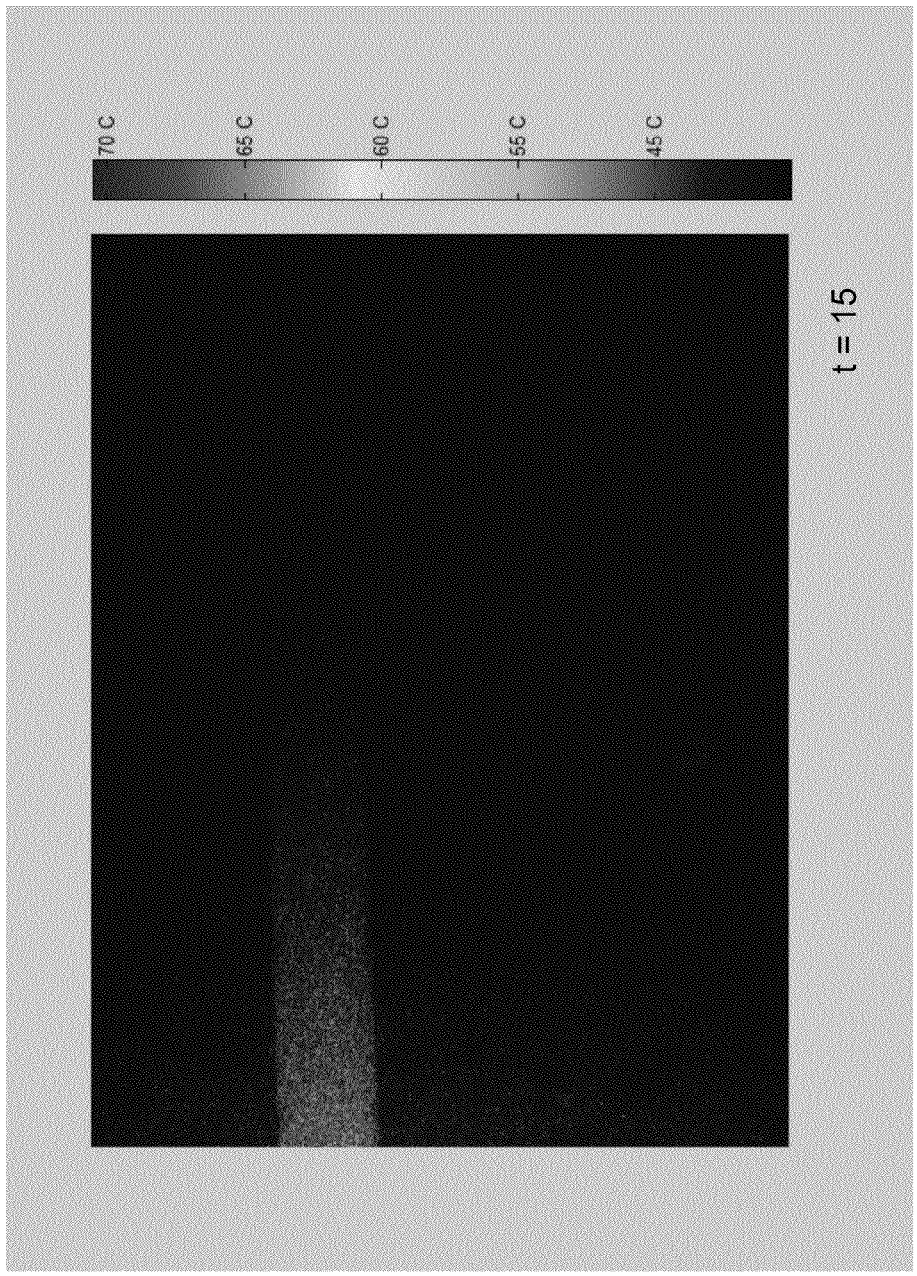
Figure 5P:
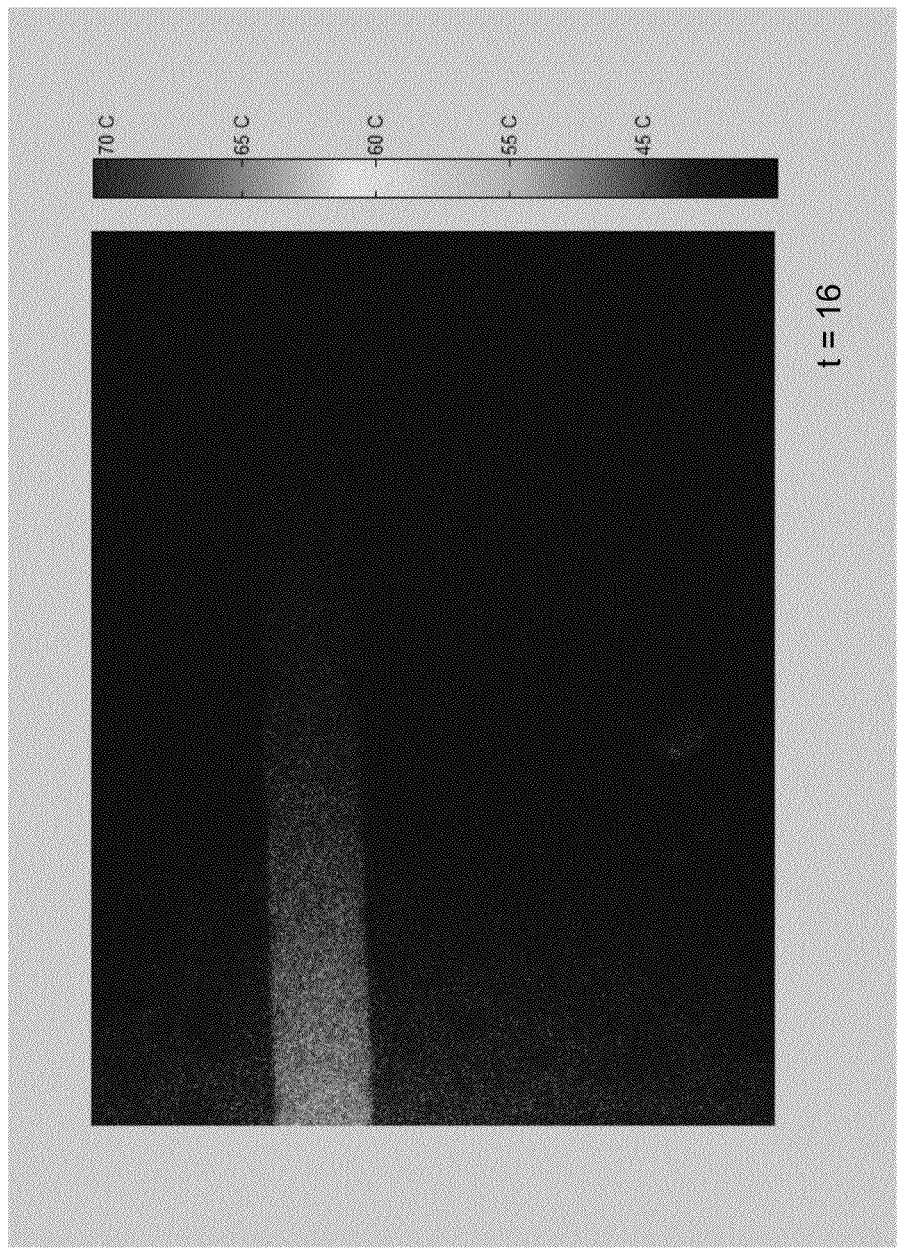
Figure 5Q:
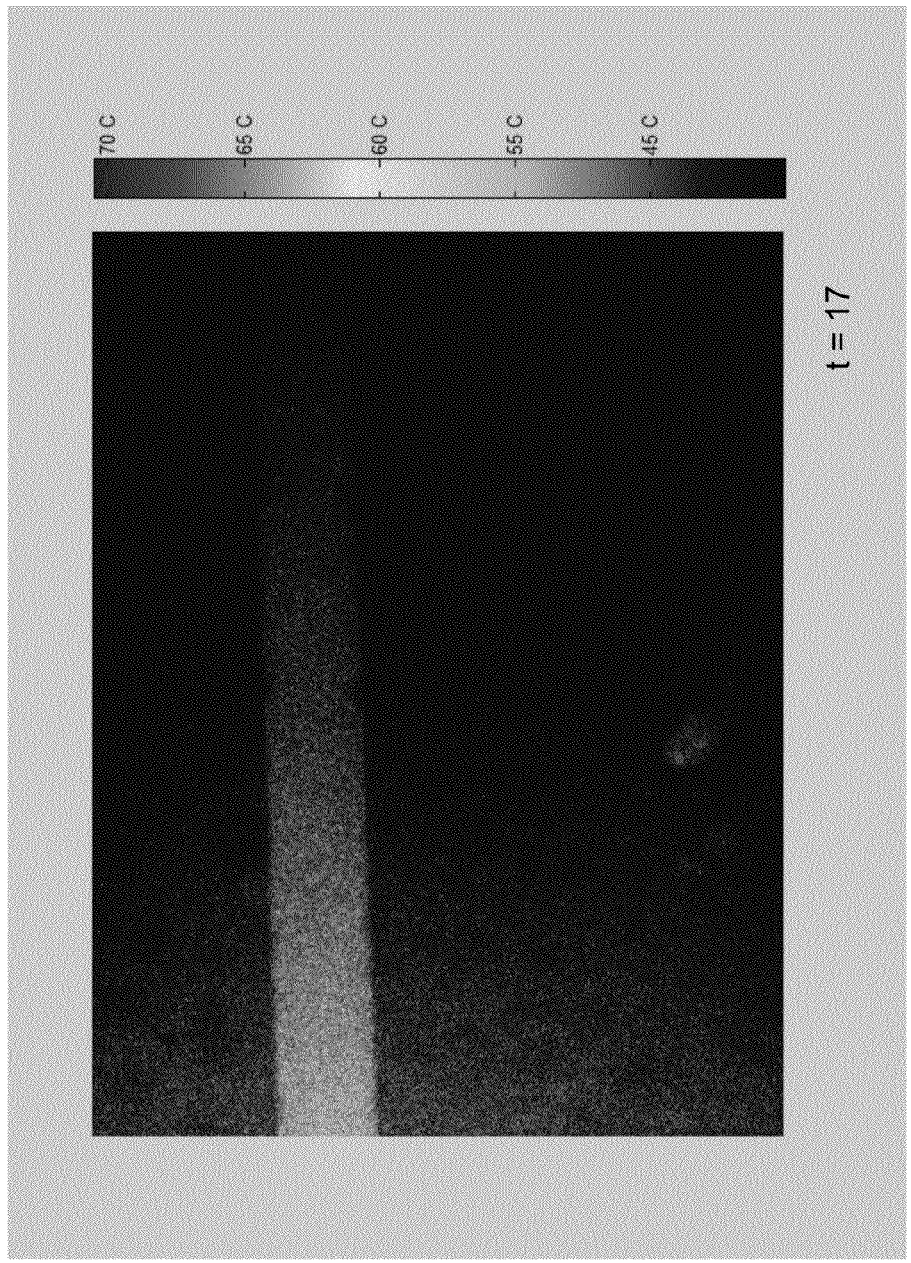
Figure 5R:
Figure 5S:
Figure 5T:
Figure 5U:
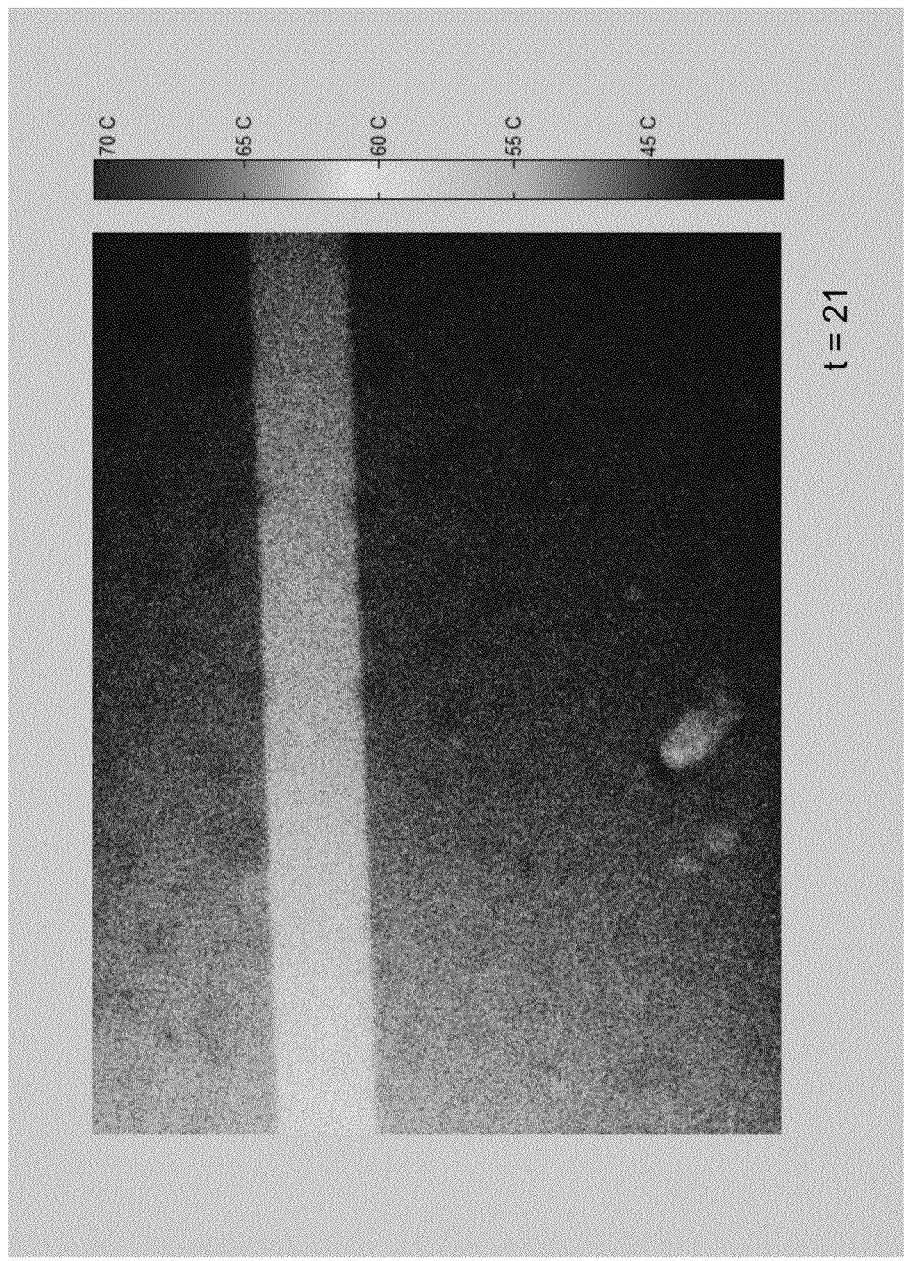
Figure 5V:
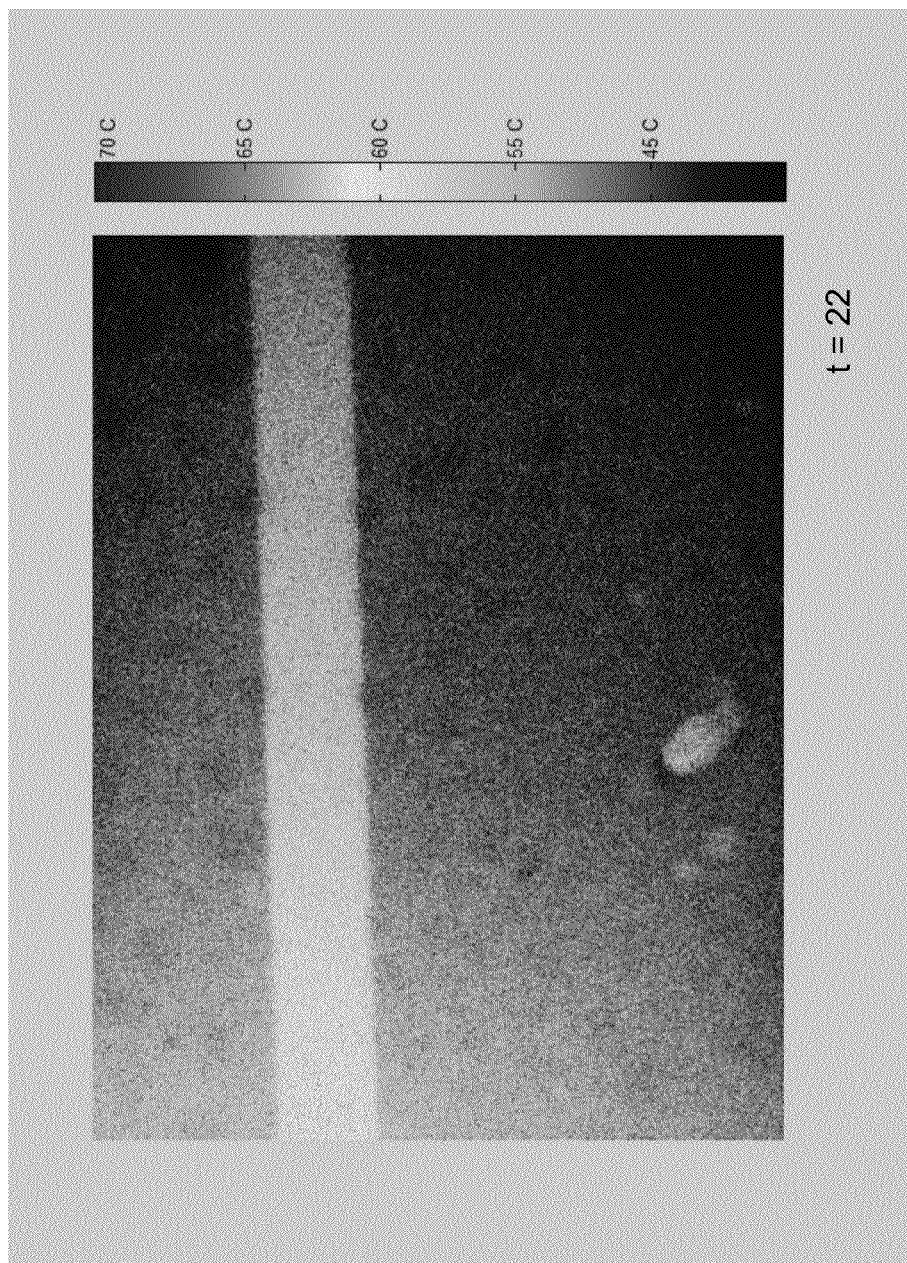
Figure 5W:
Figure 5X:
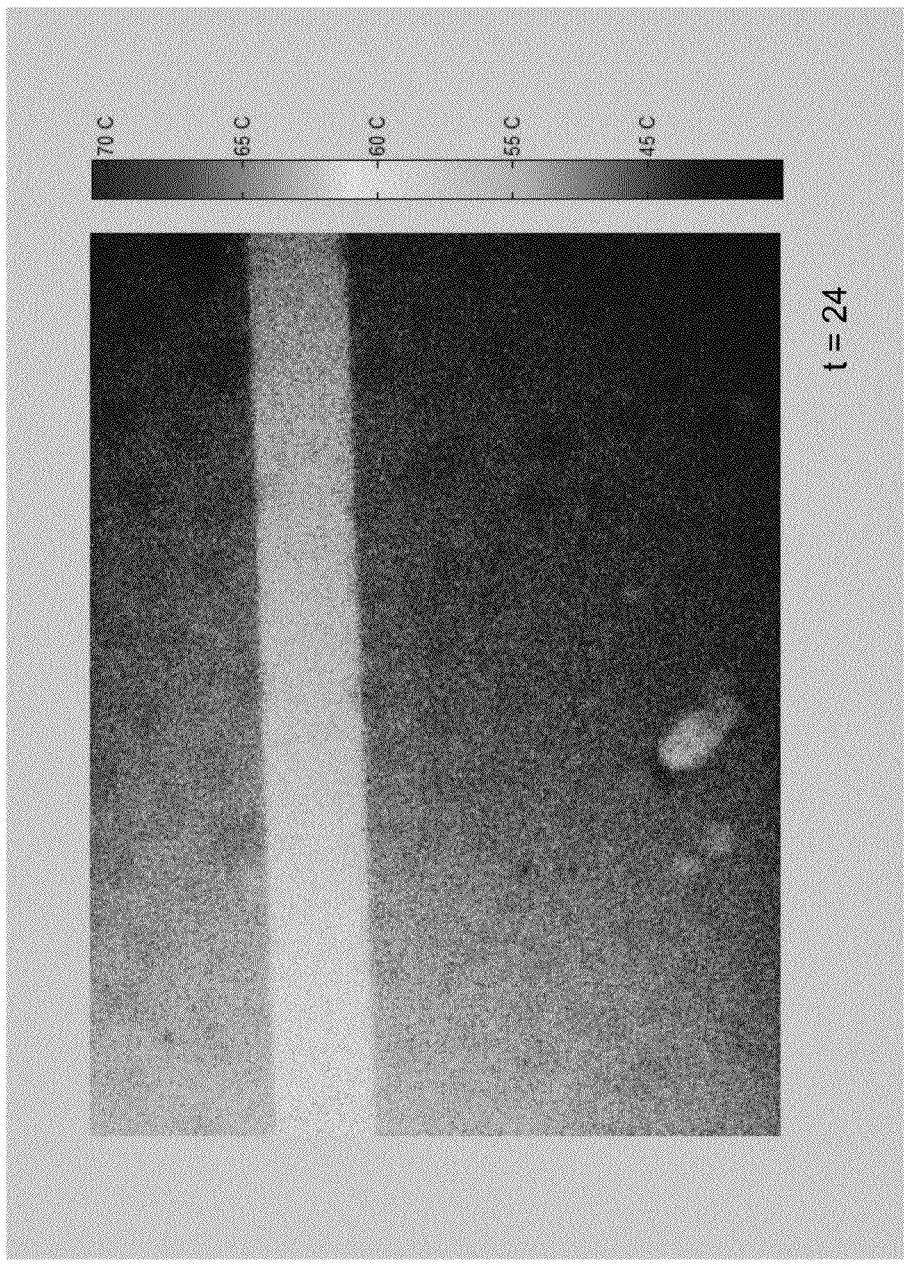
Figure 5Y:
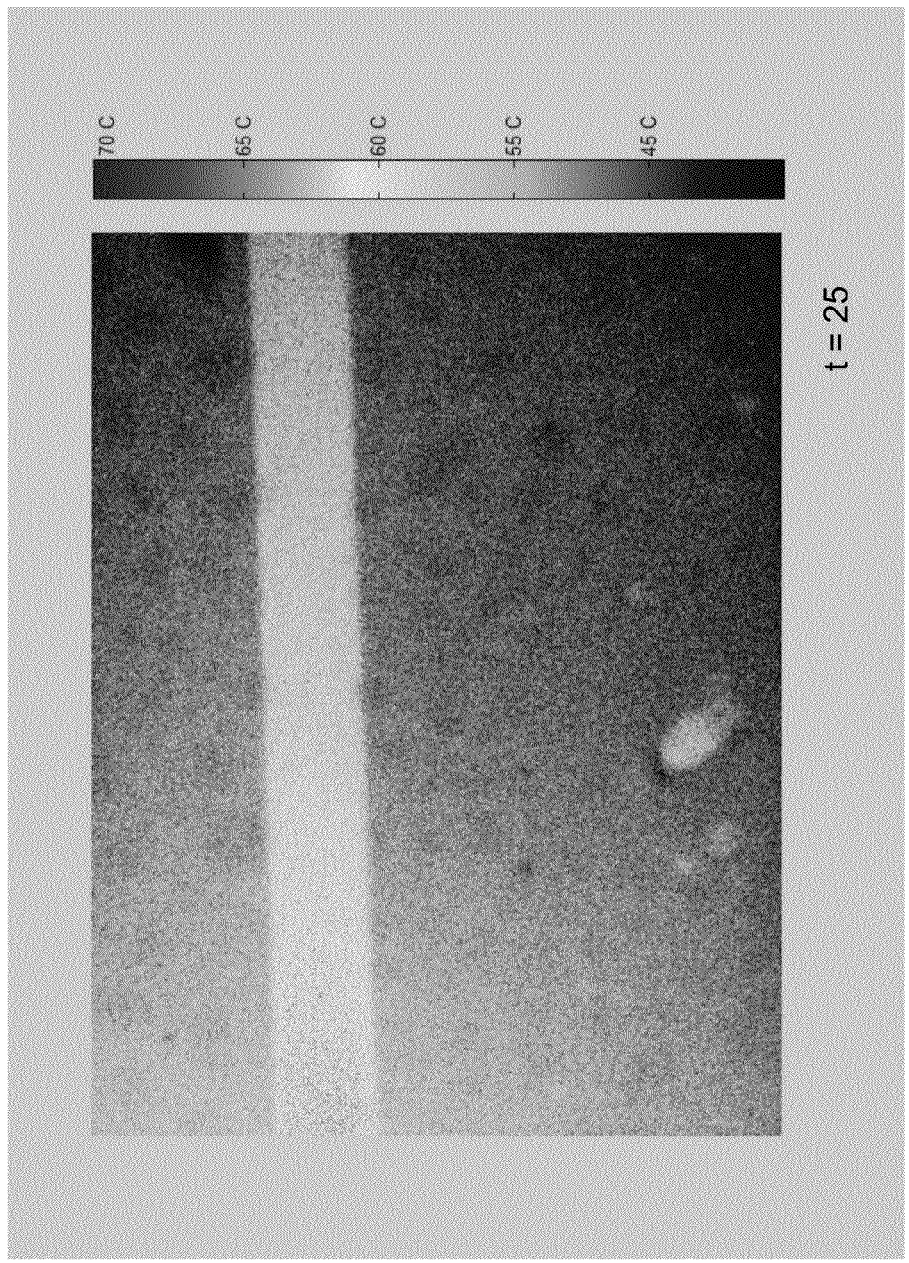
Figure 5Z:
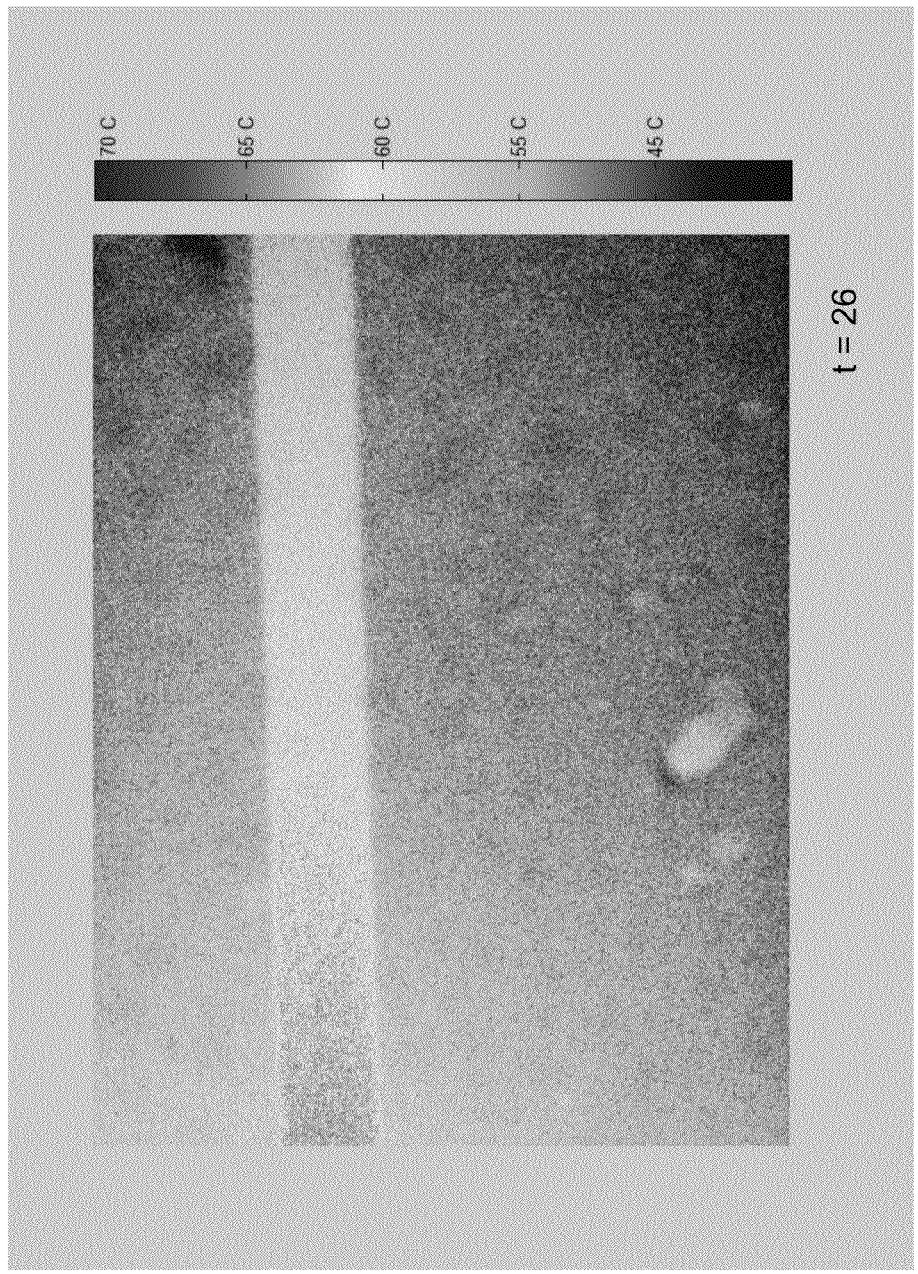
Figure 5A:
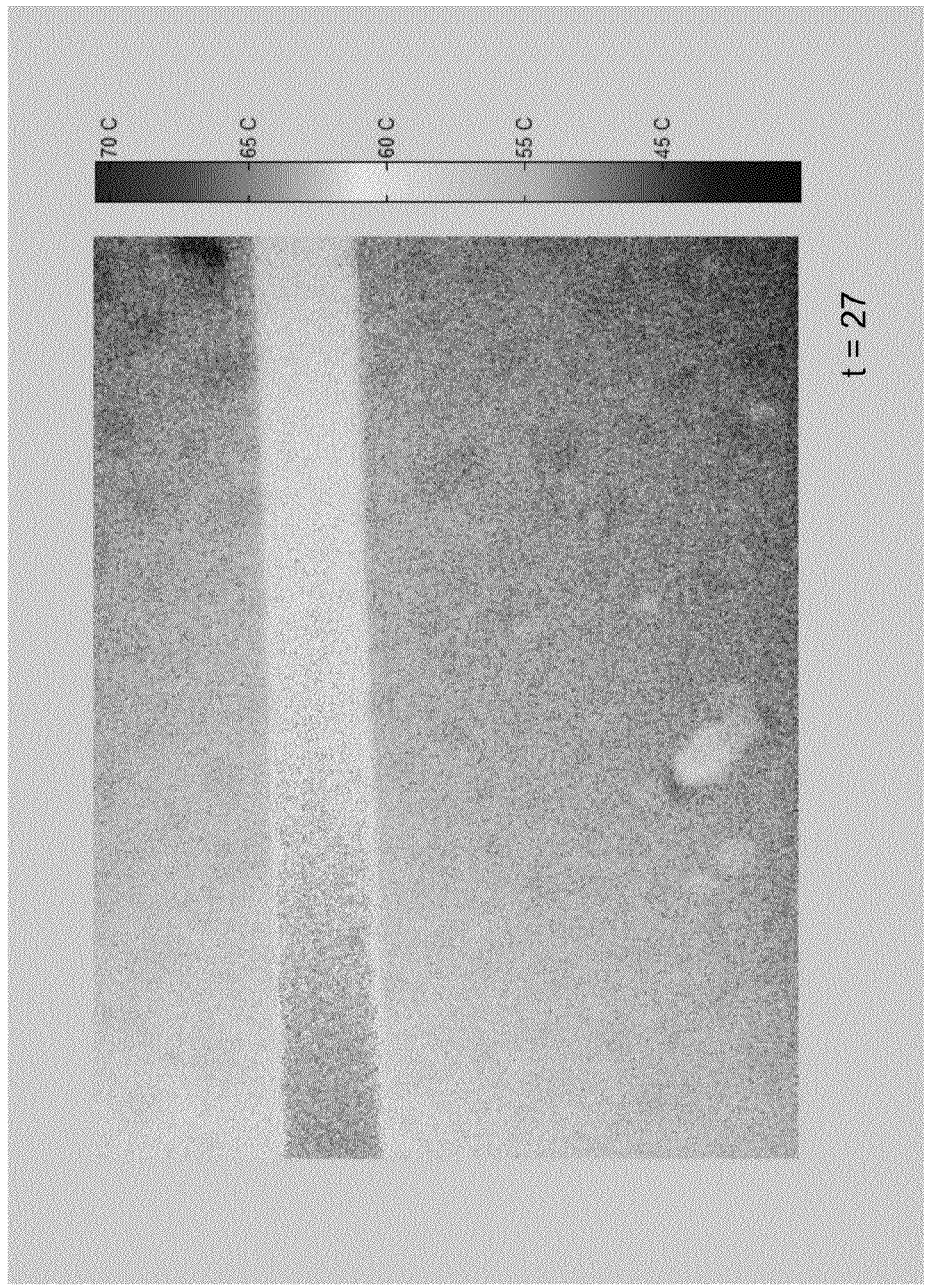
Figure 5A:
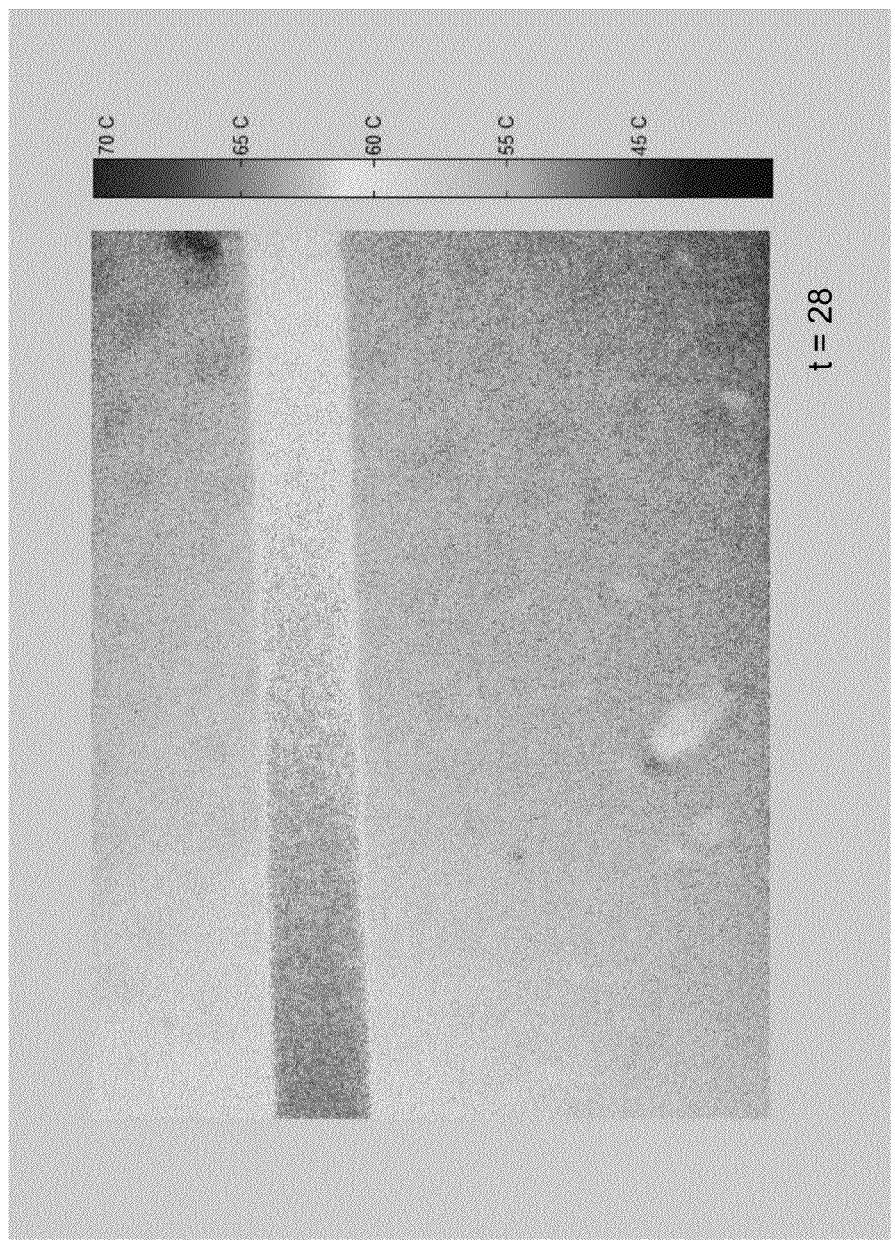
Figure 5A:
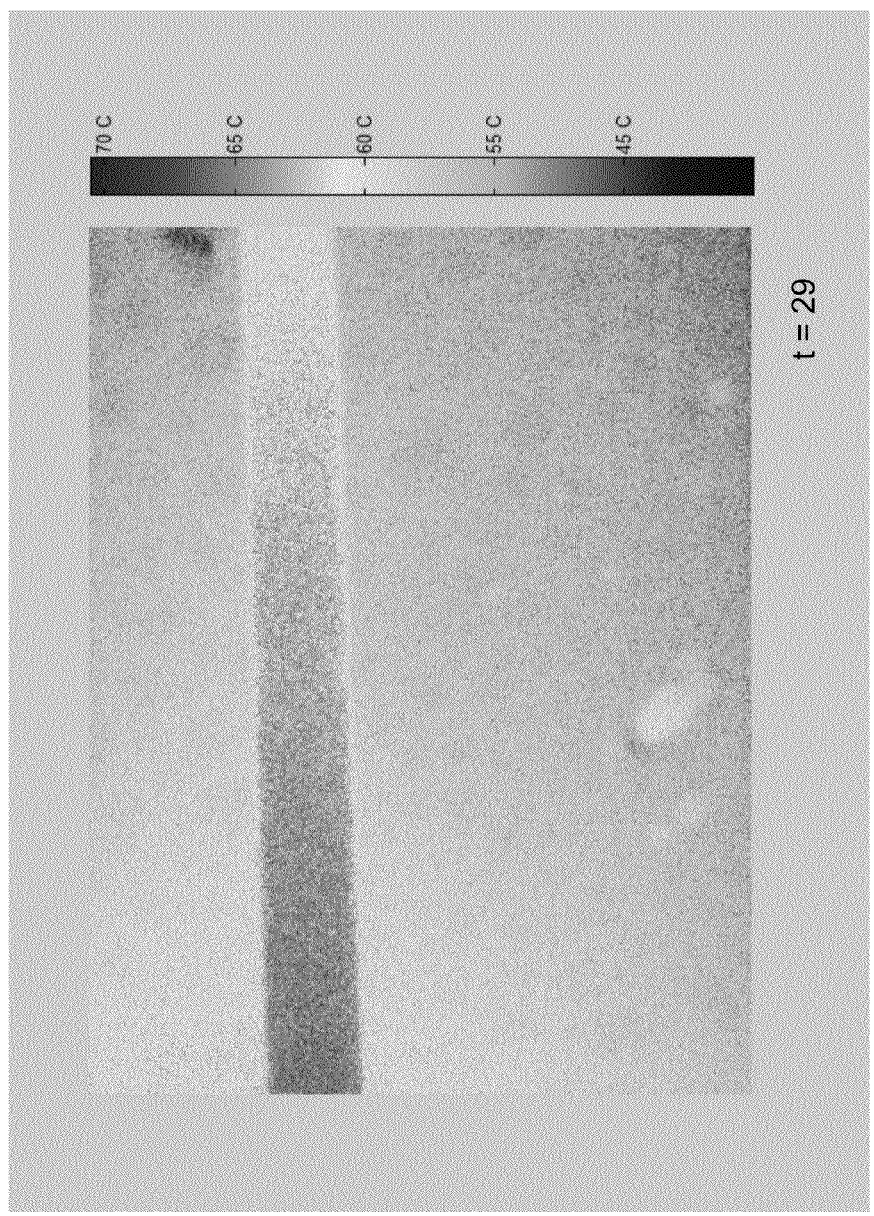

FIGS. 4A-4F are photo images from exemplary temperature sensor 100 measuring heat from a 50 um chrome resistor 112, taken at selected time intervals of 4, 9, 14, 19, 24 and 29 seconds, respectively (FIGS. 5A-5AC show the photo images of the entire range, taken at 1 frame/second for 29 seconds). FIGS. 4G-4H are plan and front view diagrams showing the configuration of temperature sensor 100 for measuring a 50 um chrome resistor, which is similar to the configuration of FIGS. 1A-1B used for calibration of the temperature sensing solution. FIG. 4I is a diagram showing a temperature versus time plot of data extracted from the images of FIGS. 4A-4F.

After calibration, the DNA temperature sensing solution can be used to measure the heat profile of custom designed chrome on glass micro-heater. Thus, an exemplary device-under-test can utilize a patterned resistor 112 situated between two electrodes 114. The contact electrodes 114 (which in this example has dimensions of 1 cm×2.5 cm) can have a sufficient heat capacity to act as heat sinks. The resistor 112 (which in this example has dimensions of 1 cm×50 µm) has a resistance suitable to create an observable thermal profile, e.g., 200Ω. To create the thermal profile, a potential, e.g., of 8V can be placed across the resistor 112, which can produce a current, i.e. 40 mA at 8V across 200Ω. Those skilled in the art will appreciate that the described dimensions and values are exemplary, and that alternative configurations can readily be chosen.

The temperature sensor 100 can be used to capture a spatially-resolved heat map, which can be captured, for example, at a rate of 1 frame/second. The results after photobleaching correction are shown in FIGS. 4A-4F. The images show the heating sinking of the centre resistor 112. Until about 13 seconds, the data obtained from the CCD sensor can be discarded, as the DNA temperature sensing solution has not yet reached the start of its active melting region. In this example, once the temperature of the viewable region reaches about 52° C., the heat sinking through the resistor 112 can be observed. The portion of the resistor 112 observable in the images is located proximate to the right electrode contact 114, and thus a heat gradient traveling generally from left to right can be seen.

The heating of the DNA temperature sensing solution itself, which can be readily observed from about 19 seconds until the end of the experiment, can be useful for many lab-on-chip based experiments, particularly those involving immersed specimens. In such experiments, knowing the heating profile of the lab-on-chip hardware, as well as the effect of such heating on the test environment, can be useful. In this example, the DNA sensing solution can double as a test load, and can reveal the heat distribution from heater through the liquid.

The thermal profile shown in FIGS. 4A-4F and FIGS. 5A-5AC demonstrates the temperature sensing properties of temperature sensor 100. A resolution of about 1 µm can be seen, with a temperature resolution of about 0.15° C. The spatial resolution can be limited by the optics being used and pixel size of the CCD array. Additionally, temperature sensor 100, using DNA oligonucleotides as the temperature sensing medium, can be considered to be highly biocompatible, and thus highly suitable for temperature sensing in biological systems.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody its principles and are thus within its spirit and scope.

What is claimed is:

1. A method for measuring temperature through a transition of one or more strands of DNA from a coupled configuration to a decoupled configuration, the method comprising:
   receiving a solution in a receptacle, the solution including the DNA as a suspension in phosphate buffered saline and a fluorescent dye adapted emit fluorescence when the DNA is in the coupled configuration;
   placing the receptacle in proximity to a surface, thereby permitting the transition of the DNA from the coupled configuration to the decoupled configuration if the temperature of the surface reaches a temperature threshold;
   acquiring a sequence of images of fluorescence emitted from the solution over a time period, each image having a plurality of regions;
   determining a plurality of fluorescence levels corresponding to each of the plurality of regions of each image;
   generating a temperature map based on the determined fluorescence levels for each image over the time period; and
   obtaining a thermal profile of the surface over the time period from the generated temperature maps for each image.

2. The method of claim 1, wherein the receptacle comprises a polydimethylsiloxane gasket disposed about the perimeter of the receptacle.

3. The method of claim 1, further comprising focusing the emitted fluorescence onto the imaging device using an optical element.

4. The method of claim 1, wherein the solution comprises 1 part of fluorescent dye and about 1 part of 800 µM of DNA strands in 1× phosphate buffered saline.

5. The method of claim 1, further comprising filtering a light source using an excitation filter to emit an excitation light.

6. The method of claim 5, further comprising optically coupling the excitation light with the receptacle using a reflective element.

7. The method of claim 5, further comprising focusing the excitation light onto the receptacle using an optical element.

8. The method of claim 5, further comprising directing the excitation light towards the solution using a reflective element.

9. The method of claim 5, further comprising focusing the excitation light onto the solution using an objective lens.

10. The method of claim 1, further comprising filtering noise from the emitted fluorescence with an emission filter.

11. The method of claim 1, wherein acquiring the image of the emitted fluorescence further comprises focusing the emitted fluorescence onto an imaging device using an ocular lens.

12. The method of claim 1, further comprising preparing the solution by combining about 1 part of the fluorescent dye with about 1 part of 800 μM of DNA strands in 1× phosphate buffered saline.

13. The method of claim 1, further comprising preparing the DNA comprising an oligonucleotide sequence consisting of AAAGGAAAGGAAAAGGAAAAGG (SEQ ID NO: 1) and/or a reverse complement thereof.

14. The method of claim 1, wherein the temperature map has a temperature range between about 10° C. and 95° C.

15. The method of claim 1, wherein the temperature map has a temperature range between about 10° C. and 25° C.

16. The method of claim 1, wherein the temperature map as a temperature range of about 10° C.

17. The method of claim 1, wherein the temperature range is centered at a temperature of 72.6° C.

18. The method of claim 1, wherein the temperature map has a resolution of about 0.15° C.

19. The method of claim 1, wherein the surface comprises a resistor.

20. The method of claim 1, wherein the surface comprises a lab-on-chip hardware component.

\* \* \* \* \*